US012751744B2

(12) United States Patent
Peterson et al.

(10) Patent No.: US 12,751,744 B2
(45) Date of Patent: Oct. 6, 2026

(54) SURGICAL IMPLANT INSTRUMENTS AND METHODS OF USE

(71) Applicant: MEDOS INTERNATIONAL SARL, Le Locle (CH)

(72) Inventors: Joseph Peterson, South Dartmouth, MA (US); Joseph M. DeLage, Berkley, MA (US); Ryan T.F. Andrade, Plymouth, MA (US); Paul S. Maguire, Hope Valley, RI (US); Ellen Roberts, Mendon, MA (US); Michael Sorrenti, Middleboro, MA (US); Roman Lomeli, Plymouth, MA (US); Benjamin Robert Powers, Columbia City, IN (US); Keanan Smith, Mansfield, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 232 days.

(21) Appl. No.: 18/466,179

(22) Filed: Sep. 13, 2023

(65) Prior Publication Data

US 2024/0081876 A1 Mar. 14, 2024

Related U.S. Application Data

(60) Provisional application No. 63/406,165, filed on Sep. 13, 2022.

(51) Int. Cl.

*A61B 17/70* (2006.01)
*A61B 17/00* (2006.01)

(52) U.S. Cl.

CPC ..................... *A61B 17/7076* (2013.01); *A61B 2017/00464* (2013.01); *A61B 2017/00477* (2013.01)

(58) Field of Classification Search

CPC ......... A61B 17/7076–17/7089; B25B 23/0021
See application file for complete search history.

(56) References Cited

U.S. PATENT DOCUMENTS 6,726,692 B2 4/2004 Bette
7,922,724 B2 4/2011 Lim
(Continued)

FOREIGN PATENT DOCUMENTS

WO 2010045301 A1 4/2010
WO 2011110916 A1 9/2011
(Continued)

OTHER PUBLICATIONS

International Search Report and Written Opinion for Application No. PCT/EP2023/075193 date of mailing Mar. 7, 2024 (18 pages).

*Primary Examiner* — Julianna N Harvey
(74) *Attorney, Agent, or Firm* — Flaster Greenberg PC

(57) ABSTRACT

Surgical instruments for interfacing with implants can include an inserter configured to dock to a unilateral portion of an implant. The inserter can include a control shaft that is configured to lock or unlock the inserter coupling with the implant. Actuation of the control shaft can occur by way of a knob that can control movement of the control shaft. The inserter can facilitate positioning of the implant relative to a surgical site and allow for application of counter-torque when imparting torque for tightening a set screw, etc. Additional instruments can also be used to manipulate the implant. For example, auxiliary instruments can be coupled to the inserter, such as a reducer instrument, to facilitate rod reduction, etc. Alternatively or in addition, a holder instrument can be used that has a threaded distal engagement feature for coupling to the implant to facilitate positioning thereof.

18 Claims, 32 Drawing Sheets

(56) References Cited

U.S. PATENT DOCUMENTS

| | | | | |
|---|---|---|---|---|
| 8,246,625 | B2 | 8/2012 | Miller et al. | |
| 8,556,903 | B2 | 10/2013 | Miller et al. | |
| 8,747,409 | B2 | 6/2014 | Ichelmann et al. | |
| 8,864,767 | B2 | 10/2014 | Blain et al. | |
| 9,198,698 | B1 | 12/2015 | Doose et al. | |
| 9,498,261 | B2 | 11/2016 | McClintock | |
| 9,517,099 | B2 | 12/2016 | Bess et al. | |
| 9,801,667 | B2 | 10/2017 | Hawkes et al. | |
| 9,924,972 | B2 | 3/2018 | Yue | |
| 9,968,383 | B2 | 5/2018 | Pinkie | |
| 10,568,673 | B2 | 2/2020 | Palagi et al. | |
| 10,595,920 | B2 | 3/2020 | Simpson et al. | |
| 10,736,682 | B2 | 8/2020 | Shoshtaev | |
| 10,898,241 | B2 | 1/2021 | Lish et al. | |
| 10,932,824 | B2 | 3/2021 | Senegas | |
| 10,966,762 | B2 | 4/2021 | Lee et al. | |
| 11,076,895 | B2 | 8/2021 | Biedermann et al. | |
| 11,123,117 | B1 | 9/2021 | Sweeney et al. | |
| 11,191,574 | B2 | 12/2021 | Butler et al. | |
| 11,266,447 | B2 | 3/2022 | Hawkes et al. | |
| 2008/0183180 | A1 | 7/2008 | Franks et al. | |
| 2008/0195155 | A1 | 8/2008 | Hoffman et al. | |
| 2012/0191144 | A1 | 7/2012 | Peultier et al. | |
| 2013/0018419 | A1 | 1/2013 | Rezach et al. | |
| 2013/0150898 | A1* | 6/2013 | Wong | A61B 17/7041 606/279 |
| 2013/0150905 | A1 | 6/2013 | Karpowicz | |
| 2014/0257416 | A1* | 9/2014 | Meyer | A61B 17/7083 606/86 A |
| 2014/0316419 | A1 | 10/2014 | Perry | |
| 2019/0008498 | A1* | 1/2019 | McClymont | A61B 90/92 |
| 2019/0059949 | A1 | 2/2019 | Ziemek et al. | |
| 2019/0105085 | A1 | 4/2019 | Hawkes et al. | |
| 2019/0183541 | A1* | 6/2019 | Lee | A61B 17/7076 |
| 2019/0183542 | A1* | 6/2019 | Lish | A61B 17/7083 |
| 2019/0274741 | A1 | 9/2019 | Vazifehdan et al. | |
| 2020/0054362 | A1 | 2/2020 | Peultier et al. | |
| 2022/0125486 | A1 | 4/2022 | Kim et al. | |
| 2022/0280207 | A1 | 9/2022 | Biester et al. | |

FOREIGN PATENT DOCUMENTS

| | | | |
|---|---|---|---|
| WO | 2012127268 | A1 | 9/2012 |
| WO | 2021165944 | A2 | 8/2021 |

* cited by examiner

SURGICAL IMPLANT INSTRUMENTS AND METHODS OF USE

CROSS-REFERENCE TO RELATED APPLICATIONS

This application claims the benefit of U.S. Provisional Application No. 63/406,165, entitled "Surgical Connector Instruments and Methods of Use," filed Sep. 13, 2022. The entire contents of this application are incorporated by reference herein.

FIELD

This disclosure relates generally to surgical instruments and related methods of use and, more particularly, to instruments for interfacing with implants, such as surgical connectors that couple multiple fixation rods or other elements, to facilitate various surgical procedures, including spine surgery.

BACKGROUND

Fixation systems can be used in orthopedic surgery or neurosurgery to maintain a desired spatial relationship between multiple bones or bone fragments. For example, various conditions of the spine, such as fractures, deformities, and degenerative disorders, can be treated by attaching a spinal fixation system to one or more vertebrae. Such systems may include a spinal fixation element, such as a rod, that is coupled to the vertebrae by one or more bone anchors, such as screws or hooks. The fixation system can also include various other implants, such as connectors for attaching multiple rods to one another. Once installed, the fixation system can hold the vertebrae in a desired position until healing or spinal fusion can occur, or for some other period of time.

Conventional instruments and systems have several shortcomings with respect to manipulating and handling surgical implants at a surgical site, including surgical connectors, and particularly in the case of minimally-invasive procedures or procedures that involve areas with narrow anatomical constraints, such as the lumbar or thoracic spine. For example, many handling instruments have been developed with regard to certain spinal fixation elements, such as implantable pedicle screws or rods, but comparatively fewer instruments have been developed for handling or interfacing with spinal fixation connectors that bridge between multiple spinal fixation rods or other elements. Accordingly, surgeons using connector implants are often left having to make do with instruments that are not intended to be used as needed.

Further, existing implant handling tools, such as rod holders and clamps, as well as fingers of a user's hand, may fail to provide sufficient clamping force to resist the multi-directional forces exerted on an implant as it is manipulated within the surgical site, making it difficult to position the implant. Further, insertion instruments can have considerable bulk and can limit the degree or manner in which the implant can be manipulated, impede insertion of a rod or other component into the implant, or cause other challenges. Moreover, such insertion instruments can lack several important abilities, including an ability to provide access to the implant and/or other components after implantation, to provide counter torque during assembly and final locking of a spinal fixation system, to couple with other instrumentation for various additional operations, etc.

Accordingly, there is a need for improved surgical connector instruments that allow for improved insertion and handling of surgical connectors at a surgical site.

SUMMARY

Disclosed herein are surgical instruments, systems, and related methods of use that provide improved insertion and handling of implants, such as surgical connectors, bone screws or anchors, etc., during surgical procedures. A variety of such instruments are disclosed herein and, in one embodiment, an inserter instrument can be provided for docking to a unilateral portion of an implant, such as a connector, bone screw, etc., to facilitate manipulation and insertion of the implant into a surgical site. The inserter instrument can use a knob or a locking handle to actuate a locking mechanism to toggle the inserter instrument between an unlocked configuration and a locked configuration with the connector. In some embodiments, the inserter instrument can provide counter torque during spinal rod reduction, set screw insertion, and various additional surgical procedures without decoupling the inserter instrument from the implant. The inserter instrument can also include one or more features to facilitate coupling with an auxiliary instrument. For example, a reducer instrument can be attached to the inserter instrument to facilitate rod or other fixation element reduction into the implant. The reducer instrument can include a reducer shaft disposed within a housing such that rotation of the reducer shaft can thread a proximal end of the reducer shaft through the housing to translate a distal portion into contact with a spinal rod disposed within the implant until the rod is properly reduced or seated relative to the implant. In some embodiments, a holder instrument can be coupled to the implant to facilitate insertion and handling of the implant at a surgical site. The holder instrument can include one or more thread forms, including male and female threads, to provide multiple options for coupling to the surgical implant.

In one aspect, a surgical instrument is disclosed that can include a proximal handle, as well as a distal inserter portion having an elongate body that can define a hollow interior. The distal inserter portion can have an opening for receiving a portion of the proximal handle therein. The instrument can further include a locking portion configured to engage a unilateral portion of an implant, as well as a control shaft that can be received in the hollow interior. The control shaft can be configured to translate distally to engage the implant engaged by the locking portion. The instrument can also include a knob configured to engage a proximal end of the control shaft to translate the control shaft relative to the distal inserter portion to transition the locking portion from an unlocked configuration to a locked configuration to secure the locking portion to the implant.

Any of a variety of alternative or additional features can be included and are considered within the scope of the present disclosure. For example, in some embodiments, the locking portion can further include a retractable clasp that can slide along a surface of the implant during distal translation of the control shaft to engage a groove formed therein.

In certain embodiments, transitioning to the locked configuration can include pulling the retractable clasp upward and inward to force a proximal-facing bearing surface of the clasp against a distal-facing bearing surface of the implant.

In some embodiments, the locking portion can also include one or more insertion tabs and a stop beam, the insertion tabs can engage a surface of the implant to lock thereto and the stop beam can be configured to abut the implant to prevent further translation of the control shaft.

In certain embodiments, the distal inserter portion can include one or more attachment features extending therefrom that can be configured to be received in an auxiliary instrument for coupling thereto. The one or more attachment features can include one or more pins that extend from the body of the distal inserter portion in some embodiments.

In certain embodiments, the auxiliary instrument can be a reducer instrument that can engage the one or more attachment features and the reducer instrument can have a reducer shaft received within a housing to reduce a spinal rod into the implant. In some embodiments, the housing of the reducer instrument can include one or more arms that extend therefrom, and the arms can have one or more tracks for receiving the one or more attachment features therein. In certain embodiments, the reducer instrument can include a retaining lever coupled to the housing to facilitate locking of the reducer instrument to the one or more attachment features. In some embodiments, the retaining lever can be configured to pivot relative to the housing to lock the reducer instrument to the distal inserter portion. In certain embodiments, the reducer shaft can include a drive interface configured to couple to an adapter for moving the reducer shaft relative to the housing. In some embodiments, the reducer shaft can include a proximal threaded portion and a distal translating portion, wherein rotation of the proximal threaded portion can translate the distal portion into engagement with the spinal rod. Still further, in some embodiments the instrument can provide a counter torque during spinal rod reduction.

In another aspect, a surgical instrument is disclosed that can include a proximal handle, a longitudinal shaft coupled to the handle, and an engagement feature disposed on a distal end of the shaft to engage one or more features of an implant. A sidewall of the engagement feature can define a distally-facing recess and can have an inner threaded surface configured to couple to a corresponding feature of the implant to couple the shaft to the implant.

As with the above-noted embodiments, any of a variety of alternative or additional features can be included and are considered within the scope of the present disclosure. For example, in some embodiments, the sidewall can have an outer threaded surface configured to couple to a corresponding feature of the implant to couple the shaft to the implant. In certain embodiments, the inner threaded surface and the outer threaded surface can be located on opposed surfaces of the sidewall. In some embodiments, the inner threaded surface and the outer threaded surface can be axially offset such that a distal end of the outer threaded surface is positioned proximal to a proximal end of the inner threaded surface. In certain embodiments, the sidewall can taper distally starting distal to the outer threaded surface.

In some embodiments, the sidewall can taper distally starting proximal to the inner threaded surface.

In certain embodiments, the engagement feature can include a centering pin that extends distally from the engagement feature, and the centering pin can be configured to be received in a portion of the implant.

In another aspect, a surgical method is disclosed that can include bringing a holder instrument into contact with an implant, the holder instrument having a longitudinal shaft that includes an engagement surface on a distal end thereof, and the engagement surface can have a reduced diameter portion with inner threads. The method can further include threading the holder instrument into a first corresponding feature of the implant, the first corresponding feature can be a surface that corresponds with the inner threads. The method can further include positioning the implant relative to a surgical site using the holder instrument.

As with the instruments described above, the methods disclosed herein can include any of a variety of additional or alternative steps that are considered within the scope of the present disclosure. For example, in some embodiments, the distal end of the holder instrument can include outer threads and the method can include decoupling the holder instrument from the first corresponding feature, as well as threading the holder instrument into a second corresponding feature of the implant, the second corresponding feature being a surface that corresponds with the outer threads. In certain embodiments, the second corresponding feature can include inner threads formed within a recess of the implant.

In some embodiments, threading the holder instrument into the first corresponding feature further can include engaging outer threads of a set screw with the inner threads. In certain embodiments, a centering pin of the engagement surface can be distally advanced into a recess of the set screw.

In another aspect, a surgical method is disclosed that can include coupling an inserter instrument to an implant having opposed arms that define a recess such that the inserter instrument contacts only one of the opposed arms and maintains access to the recess. The method can further include positioning the implant relative to a surgical site using the inserter instrument such that at least a portion of a fixation element is disposed within the recess of the implant. The method can also include inserting a set screw into the implant to capture the fixation element within the recess of the implant while maintaining a position of the implant using the inserter instrument.

As with the above-noted embodiments, any of a variety of additional or alternative steps are possible and considered within the scope of the present disclosure. For example, in some embodiments the method can include tightening the set screw by rotating the set screw in a first direction relative to the implant while imparting a counter-torque force to the implant using the inserter instrument.

In some embodiments, the method can further include decoupling the inserter instrument from the implant.

Further details are provided below. Any of the features or variations described herein can be applied to any particular aspect or embodiment of the present disclosure in a number of different combinations. The absence of explicit recitation of any particular combination is due solely to avoiding unnecessary length or repetition.

BRIEF DESCRIPTION OF THE DRAWINGS

The aspects and embodiments of the present disclosure can be more fully understood from the following detailed description taken in conjunction with the accompanying drawings, in which.

DETAILED DESCRIPTION

Certain example embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure. Additionally, to the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

Disclosed herein are surgical instruments, systems, and related methods of use for interfacing with implants during surgical procedures. The surgical instruments can include an inserter with a handle at a proximal end that is configured to engage a unilateral portion of an implant. The inserter can include a control shaft that is configured to move longitudinally to lock or unlock coupling with the implant. Actuation of the control shaft can occur by way of a knob that can control movement of the control shaft. The inserter can facilitate positioning of the implant relative to a surgical site and allow for application of counter-torque when imparting torque for tightening a set screw, etc. Additional instruments can also be used to manipulate an implant. For example, auxiliary instruments can be coupled to the inserter, such as a reducer instrument, to facilitate rod reduction, etc. Alternatively or in addition, a holder instrument can be used that has a threaded distal engagement feature for coupling to an implant to facilitate insertion and/or manipulation of the implant during a surgical procedure.

Figure 1A:
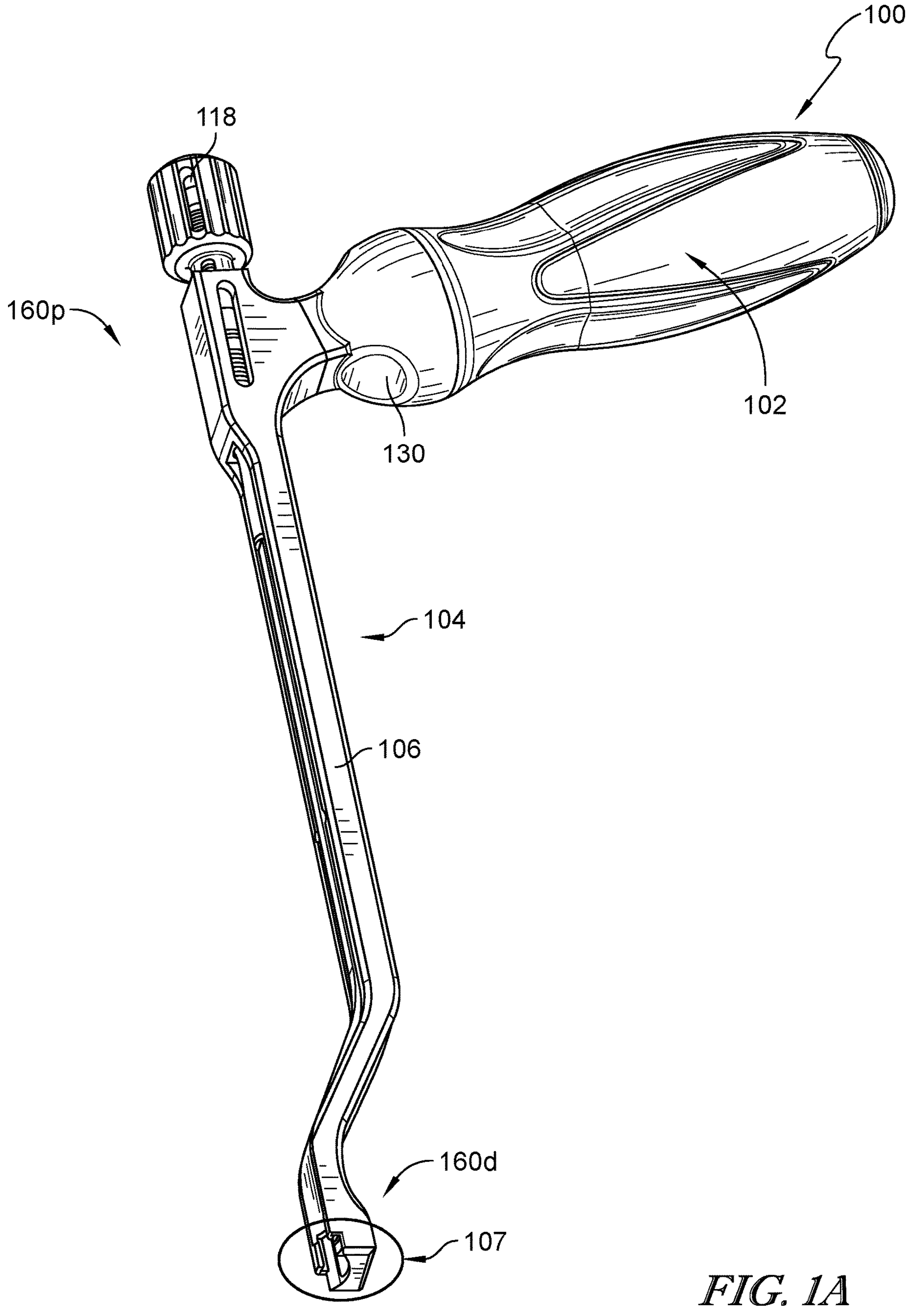
FIG. 1A is a perspective view of one embodiment of an inserter instrument.
Figure 1B:
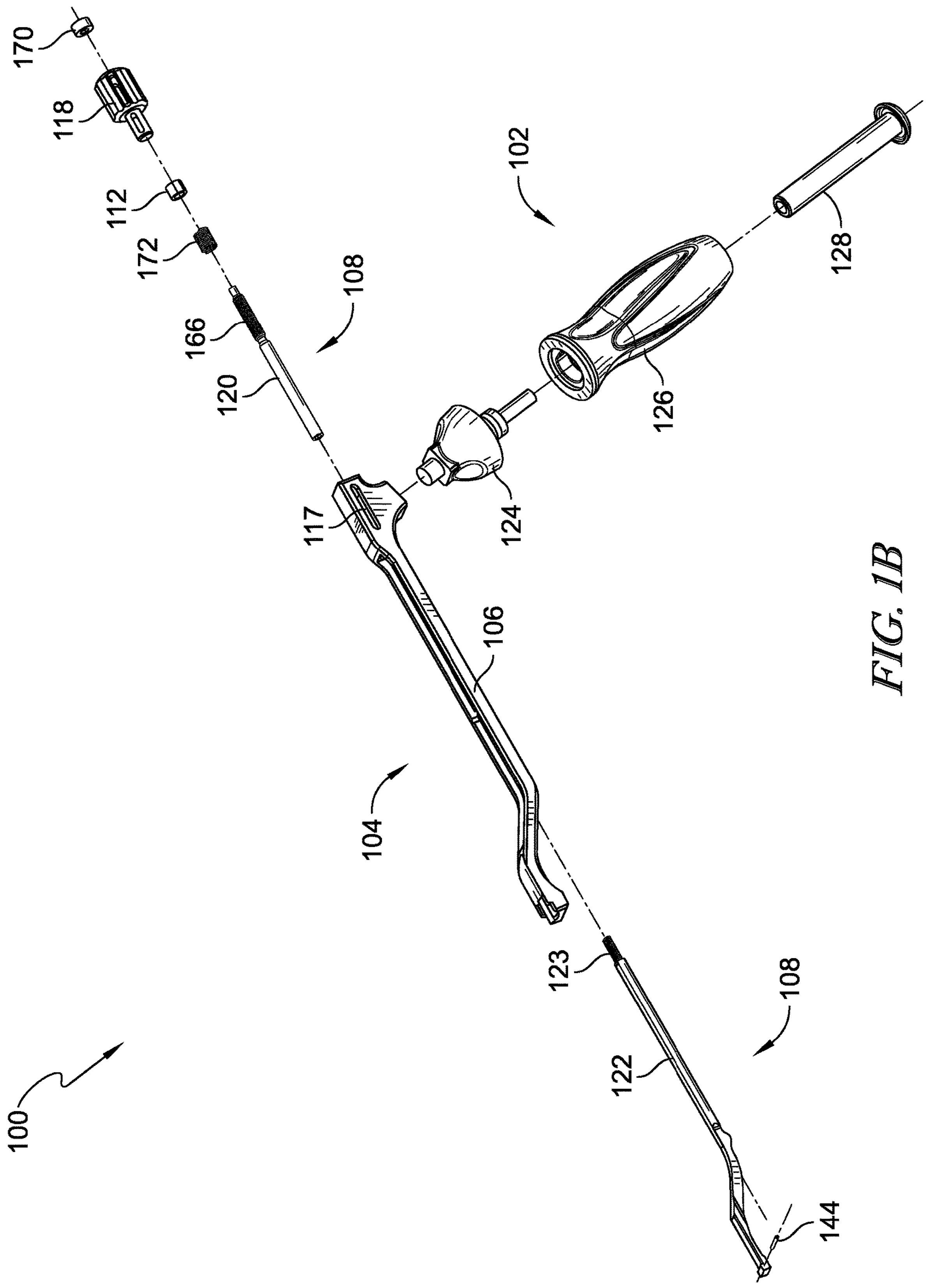
FIG. 1B is an exploded view of the instrument of FIG. 1A.
Figure 1C:
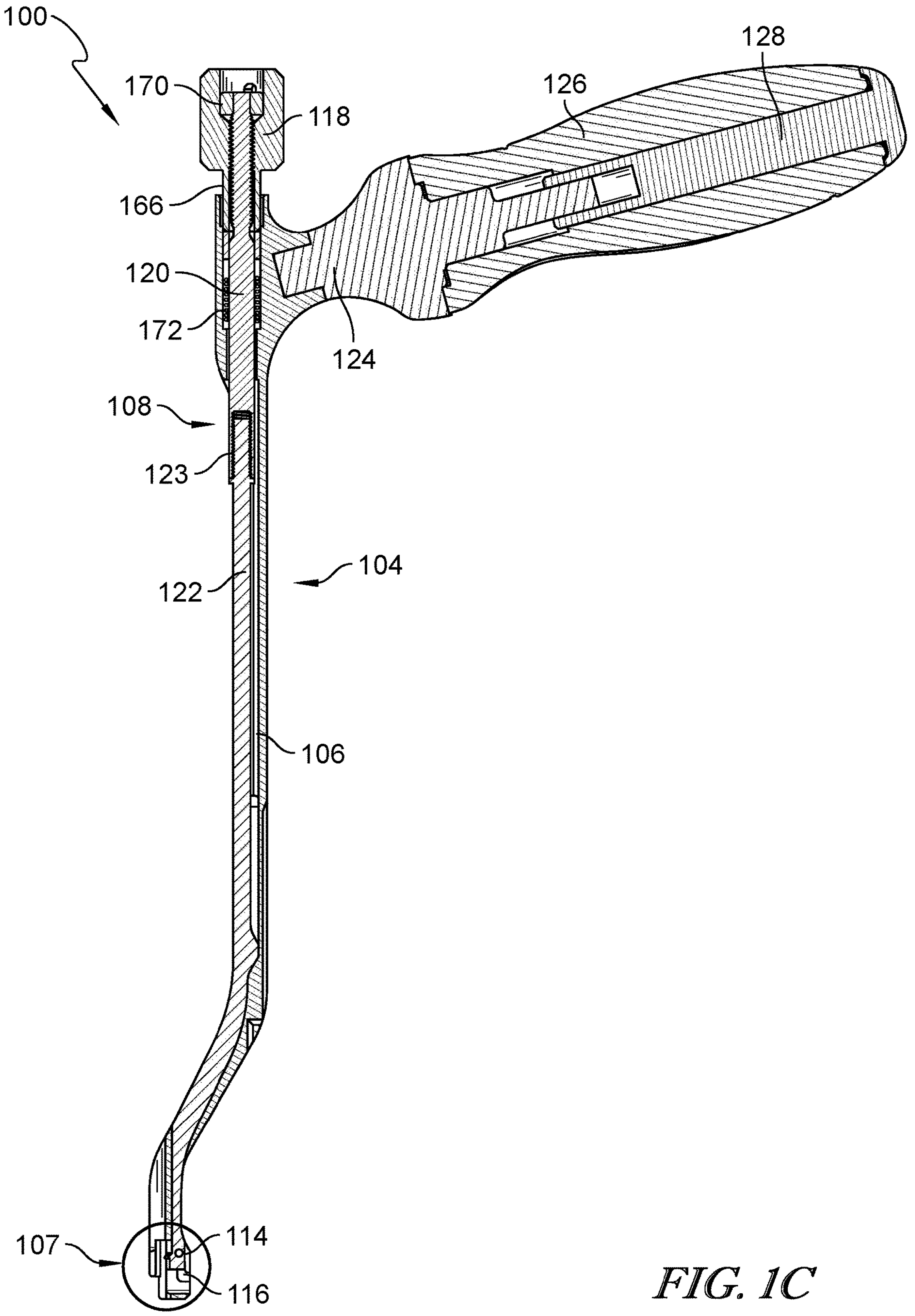
FIG. 1C is a side longitudinal cross-sectional view of the instrument of FIG. 1A.

FIGS. 1A-1C illustrate perspective, exploded, and longitudinal cross-sectional views, respectively, of one embodiment of a surgical implant inserter instrument 100. The instrument 100 can include a proximal handle 102 and a distal inserter portion 104. The inserter portion 104 can include an elongate body 106 having a proximal end coupled to the handle 102 and a distal end defining multiple locking elements 107 configured to engage a unilateral portion of an implant, e.g., a surgical connector configured to couple multiple spinal fixation rods or other elements to one another, polyaxial bone screws, other bone anchors, etc. The locking elements 107 can be configured to engage the unilateral portion of the implant, e.g., a single side of a rod slot formed in the connector, as explained in more detail below, such that the locking elements 107 mate with the connector to secure the inserter instrument to the implant to facilitate insertion and manipulation thereof. While the present disclosure often references surgical connectors, the various instruments disclosed herein can be utilized with other types of implants as well, including various screws, hooks, plates, staples, etc. Furthermore, while reference is made herein to surgical connectors being utilized to couple multiple spinal fixation rods, such connectors are also utilized to couple different spinal fixation elements. For example, in some embodiments one or both spinal fixation elements coupled by a connector can be a flexible tether.

The inserter portion 104 can include a control shaft 108 with a distal shaft portion 122 that, in combination with the locking elements 107, forms a clasp on a distal end of the instrument. The control shaft 108 can be moveably coupled to the distal inserter portion 104 by a pin 114 extending through a bore formed in a distal portion of the control shaft 108 and received within a slot or track 116 formed in the distal inserter portion 104. The control shaft 108 can include a proximal shaft portion 120 threadably coupled to the distal shaft portion 122, e.g., using male threads 123 formed on a proximal end of the distal shaft portion 122 that interface with female threads (not shown) formed along a bore in a distal end of the proximal shaft portion 120. The proximal shaft portion 120 can be disposed through a bore formed in the proximal handle 102 and can include a threaded proximal portion 166 that can couple with a knob 118. The control shaft 108 can be configured to move longitudinally relative to the inserter portion 104 in response to rotation of the knob 118 or other type of actuation control, thereby causing the clasp to lock or unlock from a surgical implant, as explained in more detail below. A proximal nut 170 or other stop can be coupled to the threaded portion 166 to prevent inadvertent removal of the knob 118 from the proximal shaft portion 120. Further, a spring 172 or other biasing element can be configured to urge the control shaft 108 proximally relative to the inserter portion 104 to provide a provisional locking force for interfacing with a surgical implant, as explained in greater detail below. A guide 112 can be disposed around the control shaft 108 between the spring 172 and the knob 118 and configured to translate without rotating, e.g., via wings that ride within slot 117 formed in the inserter portion 104. The guide can help ensure the knob does not impart any rotational forces to the spring 172 and allow smoother operation of the instrument.

The handle 102 can have a variety of forms suitable for interfacing with various users directly and/or with surgical robots or other instrumentation, e.g., manually-adjustable clamping or holding fixtures, etc. The handle 102 can be modular, such that different types of handles, e.g., handles configured for human or machine interfacing, or different sizes of handles for different users, can be utilized. Accordingly, the handle 102 can include a base 124 configured to couple to the inserter portion 104, e.g., using a post that can be received within a bore formed in the inserter portion, etc. The handle 102 can also include a gripping or interface portion 126 and a securing portion 128 that can securely couple the gripping portion 126 to the base 124. In the illustrated embodiment, the securing portion 128 extends through a bore formed in the gripping portion 126 and threadably couples to a portion of the base 124, though a variety of configurations are possible.

Figure 2A:
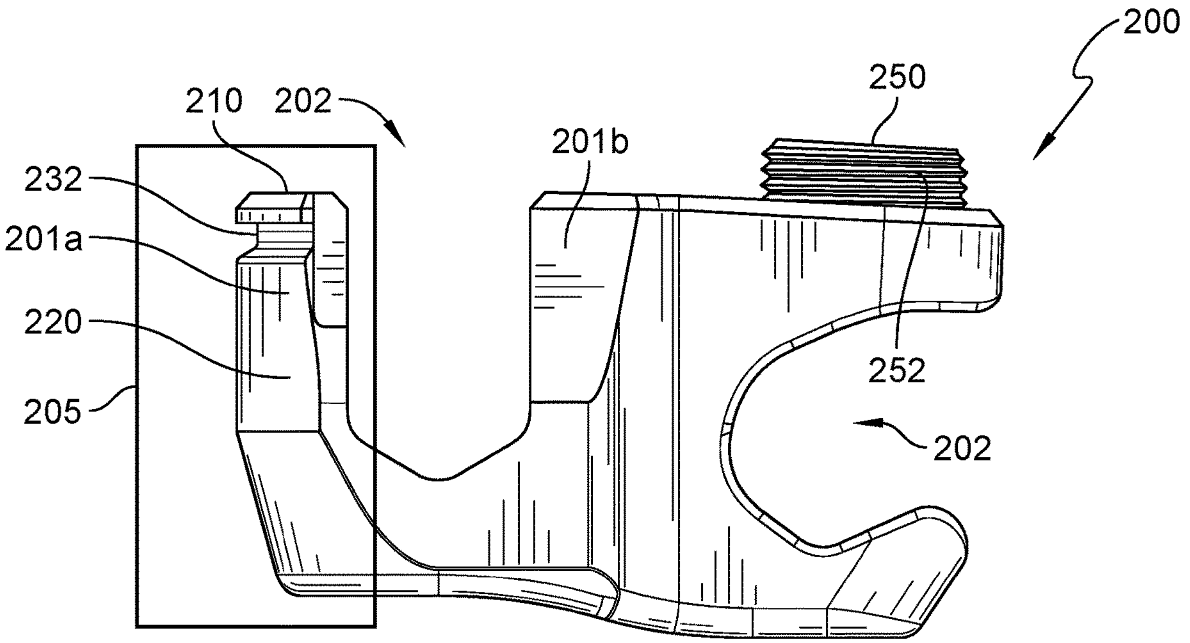
FIG. 2A is a front view of one embodiment of an implant that can be used with the instrument of FIG. 1A.
Figure 2B:
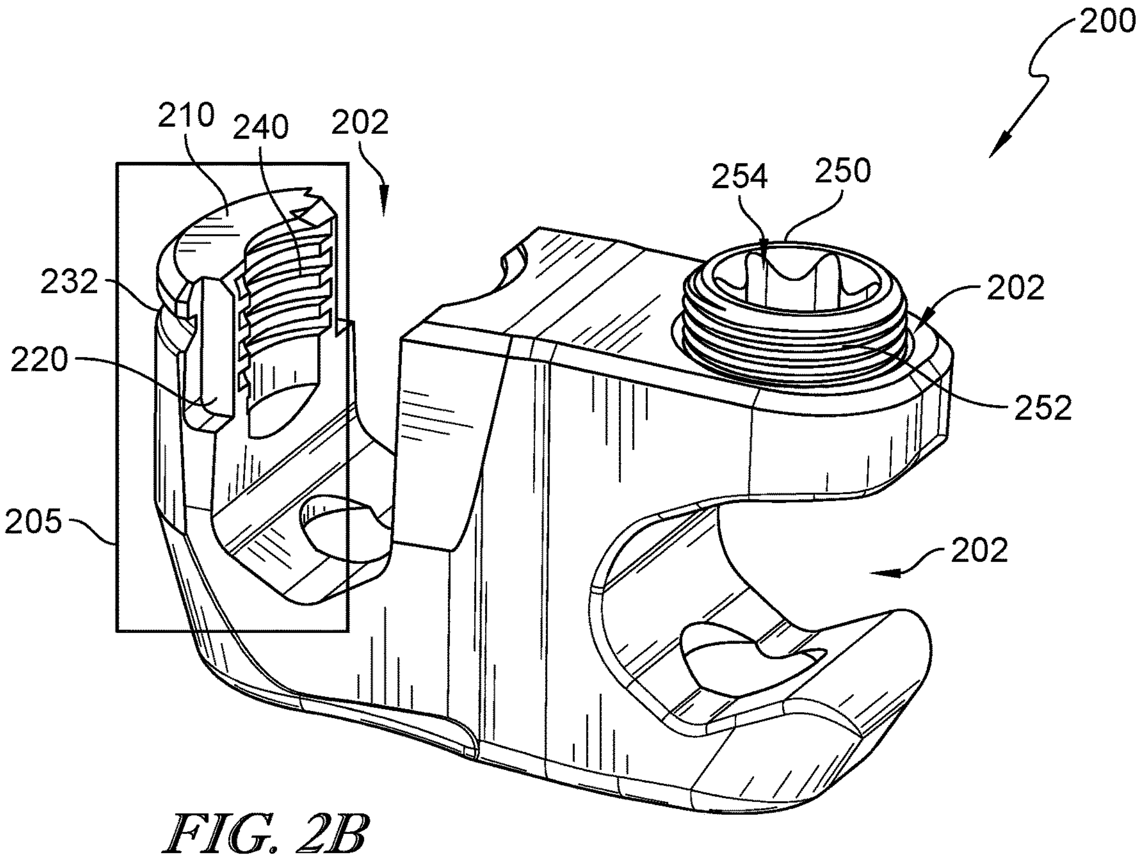
FIG. 2B is a perspective view of the implant of FIG. 2A.

FIGS. 2A-2B illustrate one embodiment of an implant, a surgical connector 200, and unilateral locking features that can interface with the distal portion of the inserter instrument 100 to allow selective coupling between the implant and the inserter instrument. Although the illustrated connector 200 is a rod-to-rod connector that bonds a plurality of rods to one another, other types of surgical connectors can be utilized as well, e.g., by incorporating the features described below to allow for coupling with the inserter instrument 100. The implant 200 can include one or more open recesses 202 formed in a body thereof (e.g., for receiving a rod and/or a set screw therethrough). For example, in some embodiments like the one illustrated in FIGS. 2A-2B, the body can include opposed arms 201*a*, 201*b* that define a recess 202 therebetween. A unilateral portion of an implant 200 may be a portion of the implant that is located towards one end of the implant or on one side of open recesses 202, e.g., the arm 201*a*. For example, the unilateral portion 205 may correspond to an end portion of the implant 200 opposing the open recesses 202 or on one side thereof. By interfacing with one side of the open recesses 202, the recesses may continue to be accessible (e.g., not blocked) after the locking elements 107 of the inserter instrument 100 are engaged in a locked configuration. This can allow, for example, a rod and/or set screw 210 to be received in one or more of the recesses 202 while coupled to the inserter instrument 100. Returning to the connector 200, it can include a set screw 250 preinstalled that can protrude proximally with threads 252 exposed. In some embodiments, the set screw 250 can be preinstalled on the connector 200, thought it will be appreciated that the set screw 250 can be added to the connector at a number of different points in a procedure. The instrument of FIGS. 13A-20, discussed below, can be utilized in some embodiments to manipulate a connector 200 by coupling to the threads 240 of the connector 200 or the threads 252 of the set screw 250 that stand proud of the connector body.

Figure 3:
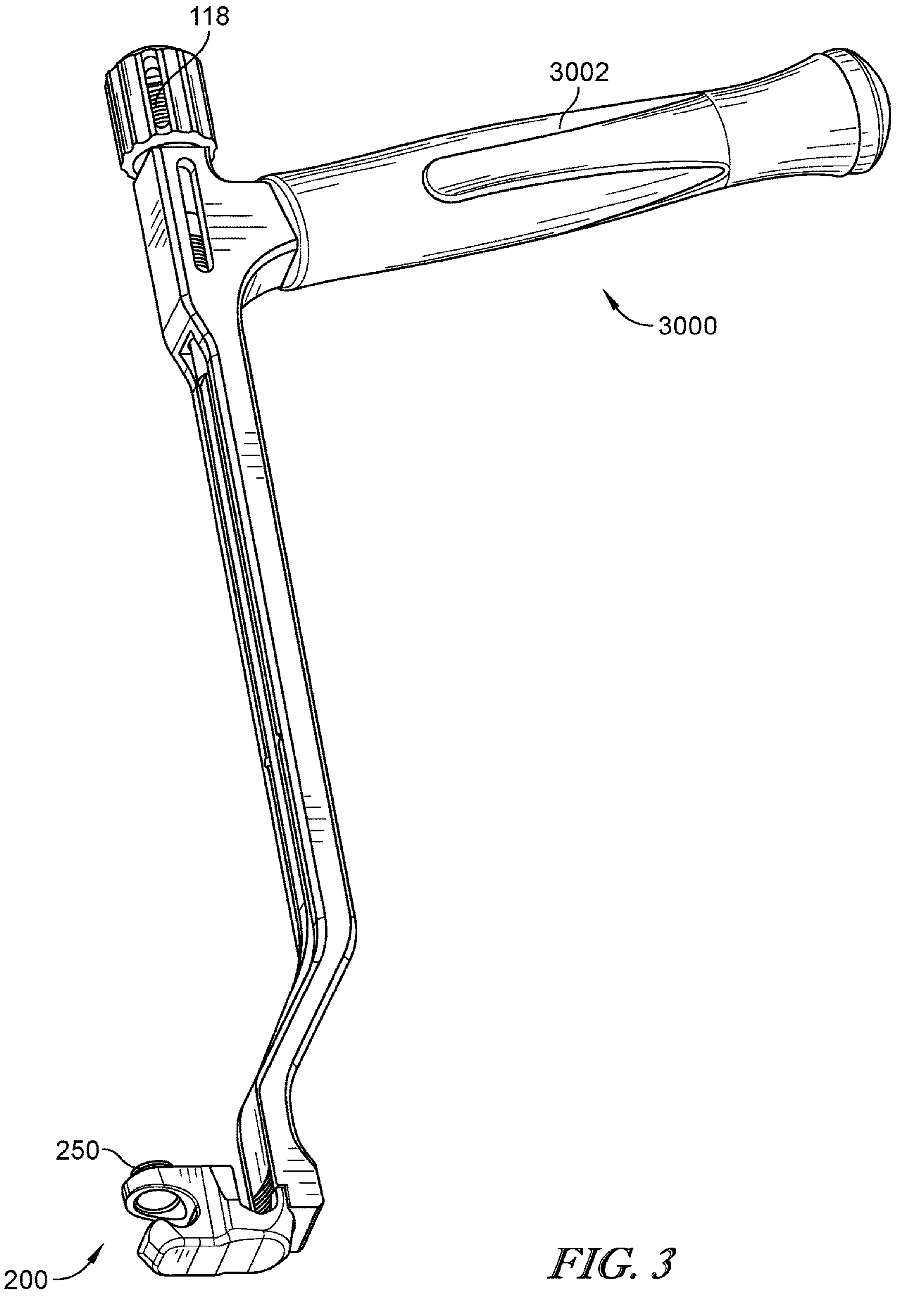
FIG. 3 is a perspective view of one embodiment of an inserter instrument coupled to the implant of FIG. 2A.

A locking interface of the connector 200 can include a top or proximal-facing bearing surface 210 and laterally-facing grooves 220. Each of these counterpart locking elements may be configured to contact, mate, interlock, or otherwise engage the locking elements 107, as shown in FIG. 3, thereby constraining movement of the connector 200 relative to the inserter instrument 100. For example, as shown in FIGS. 2A-2B, the top or proximal-facing bearing surface 210 may correspond to a top surface of the connector 200 which may partially surround the upper edge of an open recess 202. The pair of laterally-facing grooves 220 may correspond to a pair of vertical grooves formed in a sidewall of the connector adjacent to the open recess 202. The vertical grooves 220 may intersect with the recess 202, as shown in FIGS. 2A-2B, or may be spaced a distance apart from the recess 202. A distal-facing bearing surface (not shown) may also be included, e.g., a locking protrusion formed on a surface of the implant and extending transversely between the pair of vertical grooves 220. In some embodiments, the connector 200 can also include a horizontal groove or notch 232 formed along a proximal end of the unilateral portion below the top or proximal-facing bearing surface 210. Further details on connectors of the type shown in FIGS. 2A and 2B, as well as unilateral instrumentation, can be found in U.S. Pat. No. 10,966,762, entitled "Unilateral Implant Holders and Related Methods," which is incorporated by reference in its entirety herein.

Figure 4A:
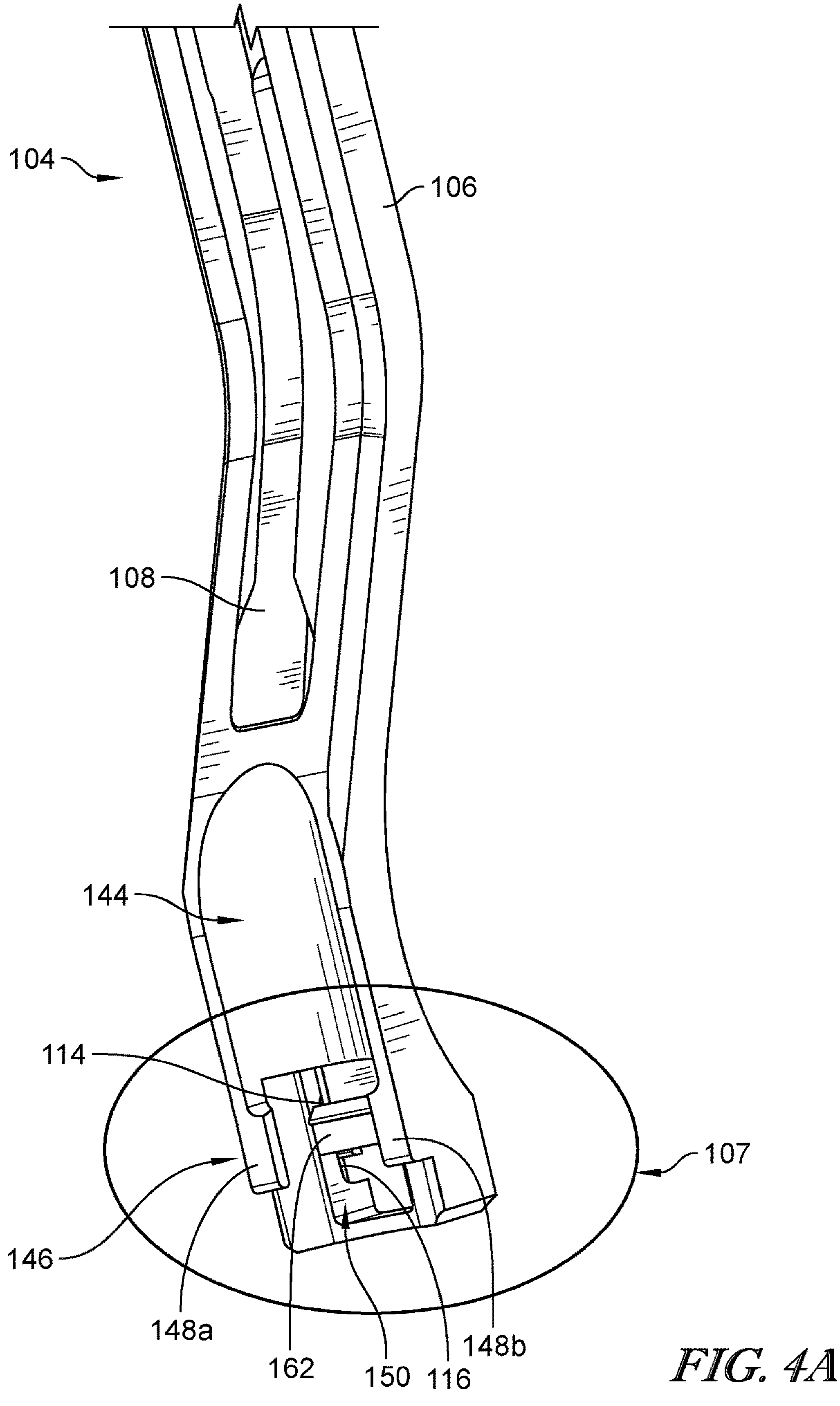
FIG. 4A is a detailed perspective view of a distal portion of the instrument of FIG. 3.
Figure 4B:
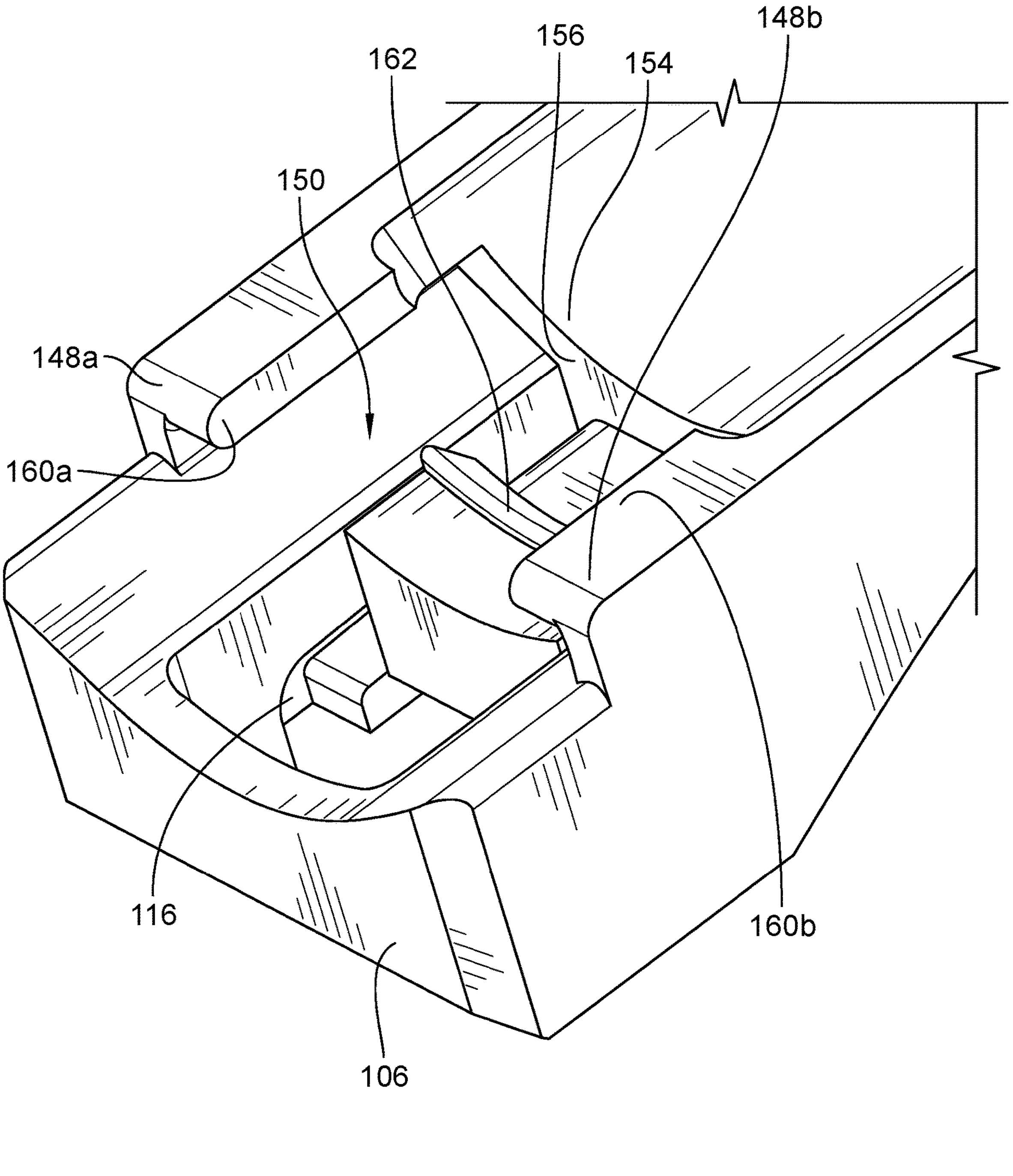
FIG. 4B is an alternative detailed perspective view of a distal portion of the instrument of FIG. 3.
Figure 4C:
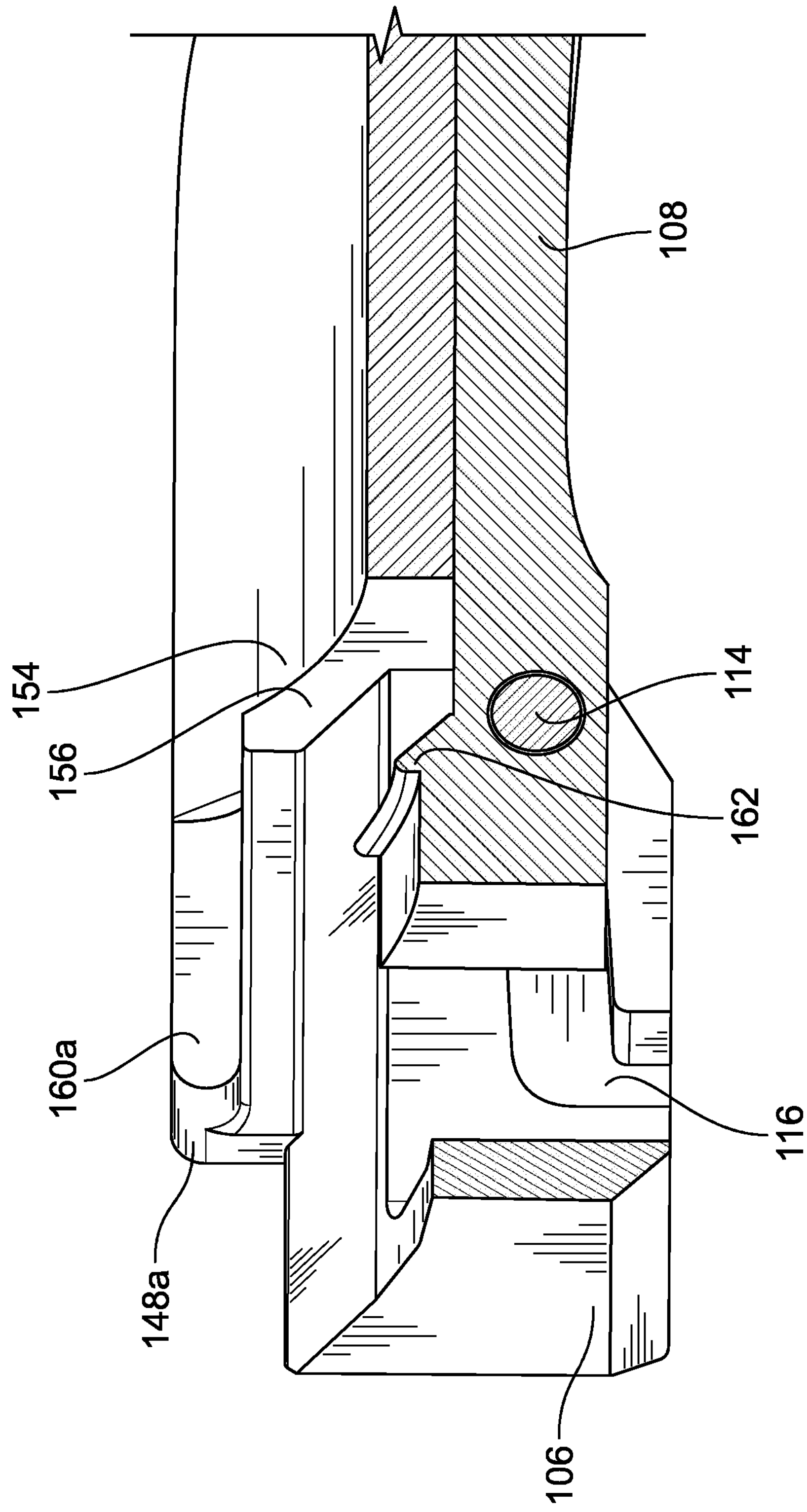
FIG. 4C is a detailed perspective longitudinal cross-sectional view of the distal portion of the instrument of FIG. 3.
Figure 5:
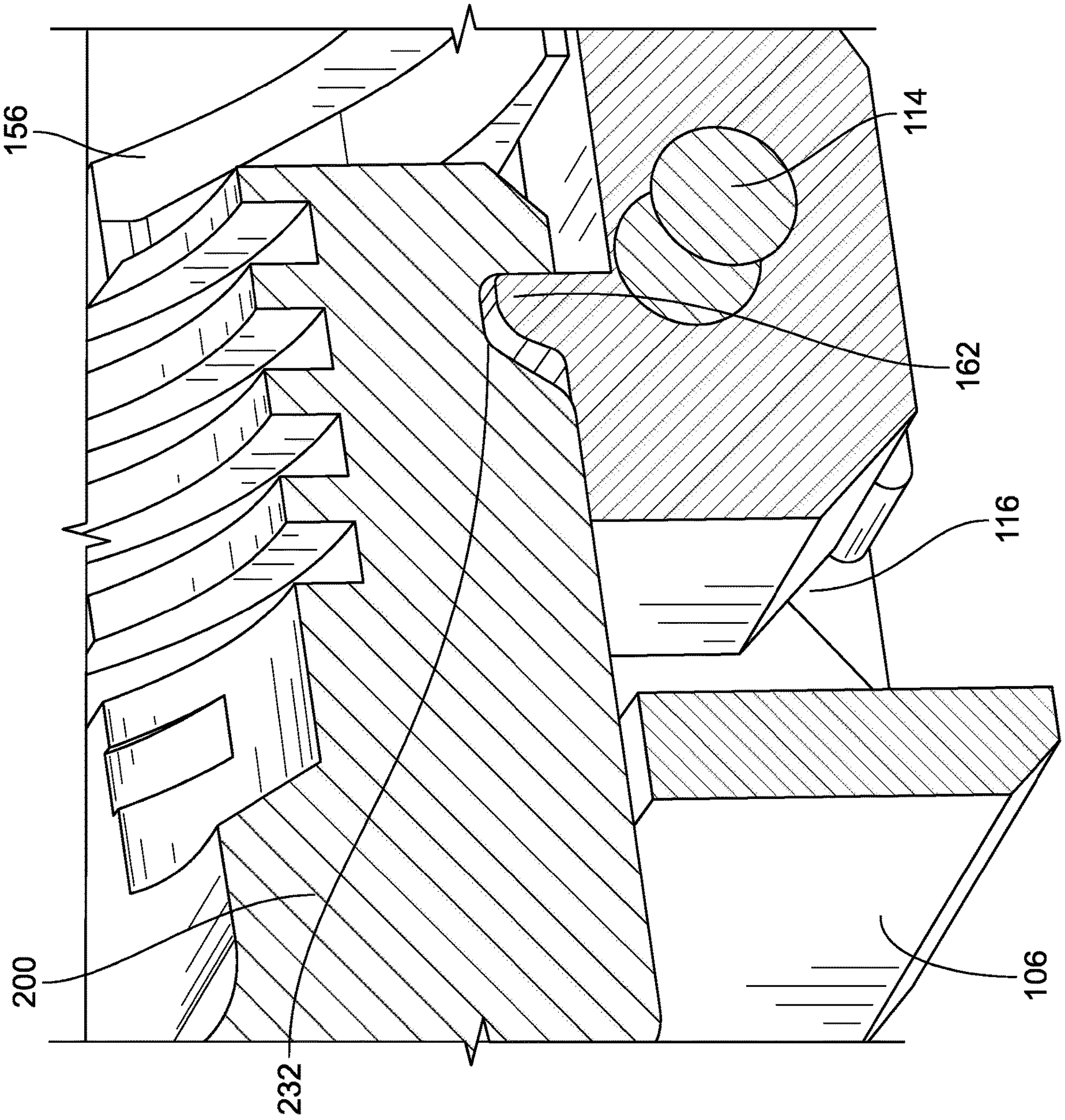
FIG. 5 is a detailed perspective longitudinal cross-sectional view of coupling between the inserter instrument and implant of FIG. 3.

FIGS. 3-5 illustrate an inserter instrument 3000 coupled to a connector 200 in greater detail. The inserter instrument 3000 can be similar to the inserter instrument 100 in many respects. In the illustrated embodiment, for example, only the form of the handle 3002 differs from the inserter 100. Accordingly, detailed description of the inserter 3000 is omitted and reference can be made to the features illustrated in connection with the inserter 100. While the inserter instrument 3000 can be coupled to polyaxial screw heads or other implants, as discussed above, the inserter instrument 3000 is discussed below with respect to the connector 200. As shown in FIGS. 3-5, the instrument 3000 can be coupled to the unilateral portion 205 such that the locking elements 107 engage the unilateral portion 205 to secure the connector 200 in place. As discussed above and shown in more detail in FIGS. 4A-4C, the inserter portion 104 can include a recess 144 that terminates with or includes the locking elements 107 to couple with or uncouple from the connector 200. The elongate body 106 of the inserter portion 104 can terminate in a forked instrument tip 146 that can include a pair of parallel arms 148*a*, 148*b* (collectively 148). The spacing and dimensions of the arms 148 can be configured to form an implant-receiving pocket 150 between opposing faces of the arms 148. The pocket 150 can be configured to accommodate a width and a depth of the unilateral portion 205 of the connector 200.

The distal portion of the elongate body 106 of the inserter portion 104 can include a horizontal stop beam 154 that extends transversely between opposing faces of the arms 148. A height of the stop beam 154 relative to the distal end of the arms 148 may be configured to accommodate, or at least partially accommodate, the height of the unilateral portion 205 of the connector. The stop beam 154 can have a distal-facing bearing surface 156 configured to contact the top or proximal bearing surface 210 of the connector, thereby constraining longitudinal movement of the connector in a proximal direction (e.g., upward movements). The stop beam 154 can have a shape that conforms to the shape of the top bearing surface 210 of the connector. For example, where the connector top bearing surface 210 forms an outer edge of an open recess 202 for receiving a rod and/or a set screw, the forward and distal faces of the stop beam 154 can be shaped such that the stop beam 154 does not block or otherwise interfere with the open recess 202 of the connector.

The forked instrument tip 146 can include a pair of opposing insertion tabs 160*a*, 160*b* (collectively 160) that protrude longitudinally along opposing faces of the arms 148 at or adjacent to the front of the pocket 150. The insertion tabs 160 may have lateral-facing bearing surfaces configured to mate and slide along lateral-facing counterpart grooves 220 formed in the unilateral portion of the connector, thereby constraining lateral movements of the implant (e.g., side-to-side and front-to-back movements).

The locking elements 107 can include a retractable hook 162 formed along a distal portion of the control shaft 108 and disposed between the opposing faces of the arms 148 at or adjacent to the back of the pocket 150. The hook 162 can be configured to interface with the groove or notch 232 formed on the connector 200. The retractable hook 162 can be configured to move proximally relative to the inserter portion 104 and laterally toward the connector (e.g., upward and inward) as it moves from an unlocked configuration to a locked configuration in which the hook 162 is disposed within the groove 232 of the connector 200. The retractable clasp 162 can be configured to move distally relative to the inserter portion 104 and laterally away from the connector (e.g., downward and outward) as it moves from a locked configuration to an unlocked configuration where the connector can be separated from the instrument. The motion of the hook 162 relative to the elongate body 106 of the inserter portion 104 can be controlled with the shape of the track 116 that received the pin 114 disposed through a bore in a distal portion of the control shaft 108 that includes the hook 162. For example, by shaping the track 116 in a manner that ramps or is angled relative to a longitudinal axis of the inserter portion 104, a distal portion of the control shaft 108 that includes the hook 162 can be made to move in a second direction as it translates distally and proximally relative to the inserter portion.

Locking of the retractable hook 162 to the connector 200 is shown in greater detail in FIG. 5. To secure the connector 200 to the instrument 100, the retractable hook 162 can be initially positioned over a proximal end of a connector 200 or other implant such that the receiving pocket 150 is aligned with the unilateral portion 205 of the connector. As the inserter instrument 100 is advanced distally towards the connector 200, the insertion tabs 160 of the arms 148 can slide longitudinally along the lateral-facing grooves 220 of the locking interface, thereby guiding the unilateral portion 205 of the connector 200 proximally into the pocket 150.

Translation of the control shaft 108 and the hook 162 formed thereon can be controlled by rotation of the knob 118 and/or manual manipulation of the control shaft against the bias force of the spring 172. For example, once assembled, the spring 172 can impart a proximally-directed biasing force onto the control shaft 108, e.g., by virtue of its compression between the elongate body 106 of the inserter portion 104 and the guide 112, which in turn imparts a force onto the knob 118. This can provide a provisional locking force to the instrument 100, such that the control shaft 108 and hook 162 must be distally advanced over the biasing force of the spring to allow coupling with a connector 200 and, once the bias force is restored, will tend to couple with any correctly positioned connector without further user interaction.

Accordingly, in one embodiment, coupling a connector or other implant to the inserter instrument 100 can include a user distally advancing the control shaft 108 against the bias force of the spring 172, e.g., by manually pushing on the knob 118 to advance it, and the control shaft 108 threadably coupled thereto, distally. A connecter 200 or other implant can then be positioned relative to the distal end of the inserter instrument 100 such that the forked distal tip engages the lateral grooves of the unilateral portion 205 of the connector 200 or other implant. A user can then release the force utilized to overcome the biasing force of the spring 172. The spring 172 will then urge the control shaft 108 proximally relative to the inserter portion 104, which will move the hook 162 proximally to engage the groove 232 formed in the unilateral portion 205 of the connector or other implant.

To securely couple the connector 200 and the inserter instrument 100 beyond the provisional coupling provided by the spring 172, the user can rotate the knob 118 until a distal surface of the knob 118 abuts a proximal surface of the inserter portion 104. This can ensure that no distal movement of the control shaft 108 relative to the inserter portion 104 is possible, thereby locking the instrument 100 against decoupling from the connector 200.

Releasing the connector 200 or other implant from the instrument 100 can include rotating the knob 118 in an opposite direction to introduce a gap between a distal end of the knob 118 and a proximal surface of the inserter portion 104. This can return the instrument to a state of provisional locking to the connector or other implant. To decouple the connector completely, a user can again distally advance the knob 118 and control shaft 108 over the bias force of the spring 172 to clear the hook 162 from the groove 232 of the connector 200 and thereby allow separation of the connector from the inserter instrument 100.

As shown in FIG. 5, the connector 200 can advance proximally relative to the elongate body 106 of the inserter portion 104 during coupling until the distal-facing bearing surface 156 of the stop beam 154 contacts or abuts the top or proximal bearing surface 210 of the connector locking interface. Once the connector top bearing surface 210 contacts or abuts the stop beam 154, the retractable hook 162 can be engaged to lock the connector in place. To do this, the control shaft 108 can be withdrawn proximally (e.g., via the bias force from the spring 172 and/or via actuation from the knob 118). As the control shaft translates proximally relative to the inserter portion 104, the pin 114 can ride within the slot 116 of the elongate body 106 of the inserter portion 104 to control the movement of the retractable hook 162 from an unlocked configuration to a locked configuration relative to the connector. The pin 114 can be configured to protrude from at least one of the laterally opposing faces of the control shaft 108 and into the slot 116 formed in distal portion of the elongate body 106 of the inserter portion 104. As noted above, the slot 116 can include a ramped portion that extends obliquely with respect to a longitudinal axis of the instrument. Accordingly, movement of the pin 114 along the slot 116 can effect movement of the hook 162 both along a longitudinal axis of the instrument and transverse thereto (e.g., inward or outward toward or away from a central axis of the connector).

To lock the inserter instrument 100 to the connector 200 or other implant, the retractable hook 162 can be pulled upward (i.e., proximally along a longitudinal axis of the instrument 100) and inward (i.e., transversely to a longitudinal axis of the instrument 100 and toward a longitudinal axis of the connector 200) towards the locked configuration, thereby forcing the hook 162 into engagement with the groove 232 formed in the connector 200. In this locked configuration, the connector 200 can be captured and constrained from movement in all directions, thereby securely coupling the connector 200 to the inserter instrument 100 such that the instrument can be utilized to remotely manipulate the position of the connector (i.e., a user grasping the proximal end of the instrument 100 can control the position of the connector 200 coupled to a distal end of the instrument). The inserter instrument 100 can leave the recess 202 of the connector 200 unobstructed to allow a spinal rod, set screw, tether, other fixation element, etc., to be disposed therein. In some embodiments, the inserter instrument 100 can be configured to provide counter torque during insertion and tightening of a set screw 250 into the recess 202 of the connector 200. For example, as a user tightens a set screw by rotating it in a first direction (e.g., via a driver, etc.), the user can simultaneously resist rotational or other movement of the connector 200 or other implant by applying counter-torque (e.g., a force in a second direction opposite the first direction) through the inserter instrument 100. The above-noted rigid coupling between the inserter instrument 100 and the connector 200 that constrains relative movement in all directions can allow a user to apply effective counter-torque to the connector 200 via the inserter instrument 100. When a user is finished manipulating the connector 200 using the instrument 100 (including utilizing any secondary or auxiliary instrumentation as described herein), the inserter instrument 100 can be separated from the connector 200 by advancing the retractable hook 162 distally using the knob 118 and/or manual advancement of the control shaft 108 against the bias force of the spring 172 towards the unlocked configuration.

FIGS. 6A-6C and 7 illustrate another embodiment of a unilateral inserter instrument 100'. As mentioned above, the instrument 100' can be similar to the inserter instrument 100 in many respects and, as a result, a detailed description of every feature is omitted for the sake of brevity. In the inserter instrument 100', a lock handle 118' in combination with a release button 119' are provided in lieu of the knob 118 to actuate the inserter instrument 100'. The lock handle 118' can be received in a recess of the handle 102'. The lock handle 118' can include a body 120' having an extension 124' that is configured to be received in the hollow interior 121 of the inserter instrument 100'. The extension 124' can include a plurality of holes 126' therein that can receive one or more pins 129 to pivotably couple the extension 124' to the inserter portion 104' and the control shaft 108, thereby allowing control of relative movement between these components.

Figure 6A:
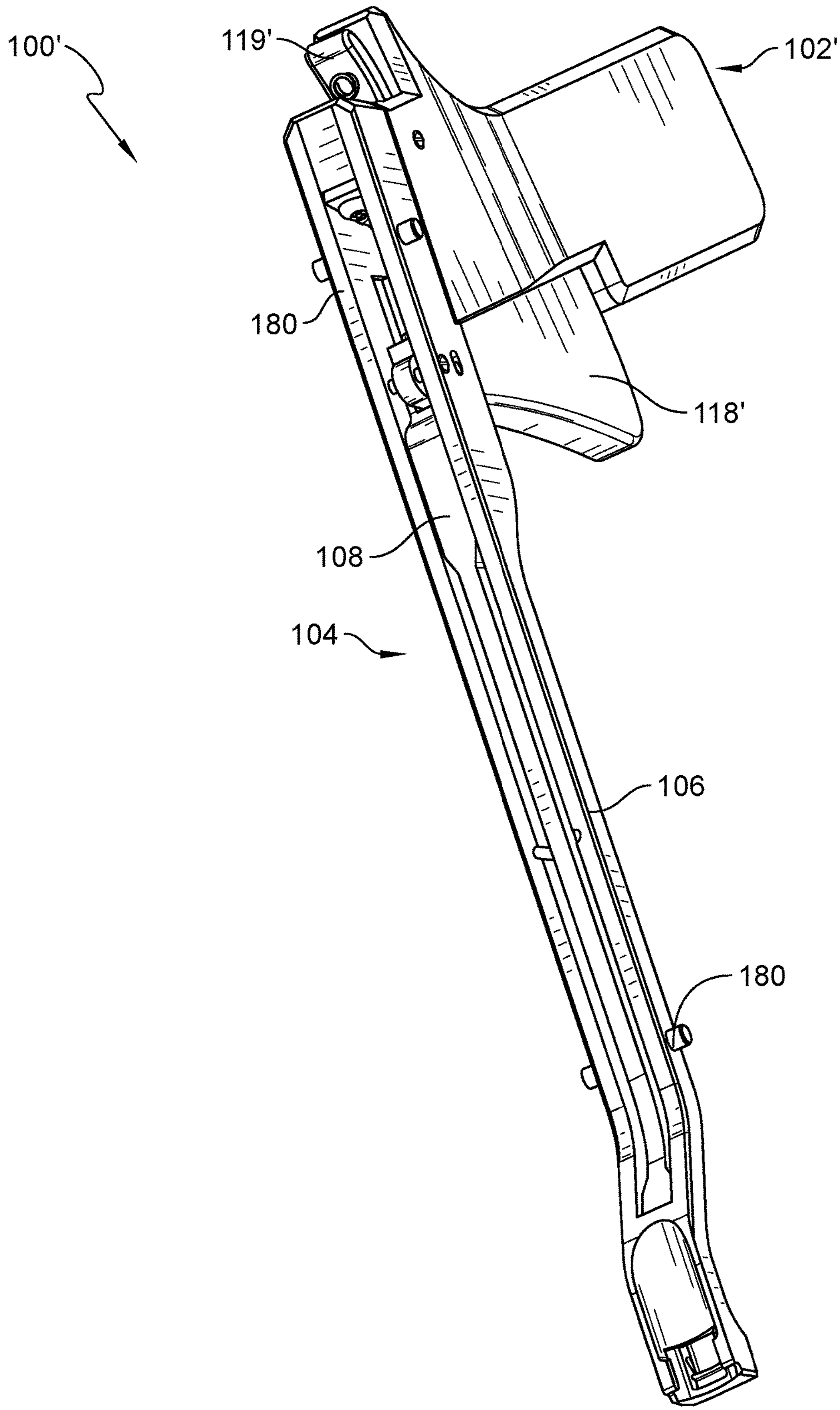
FIG. 6A is a top perspective view of one embodiment of an inserter instrument.
Figure 6B:
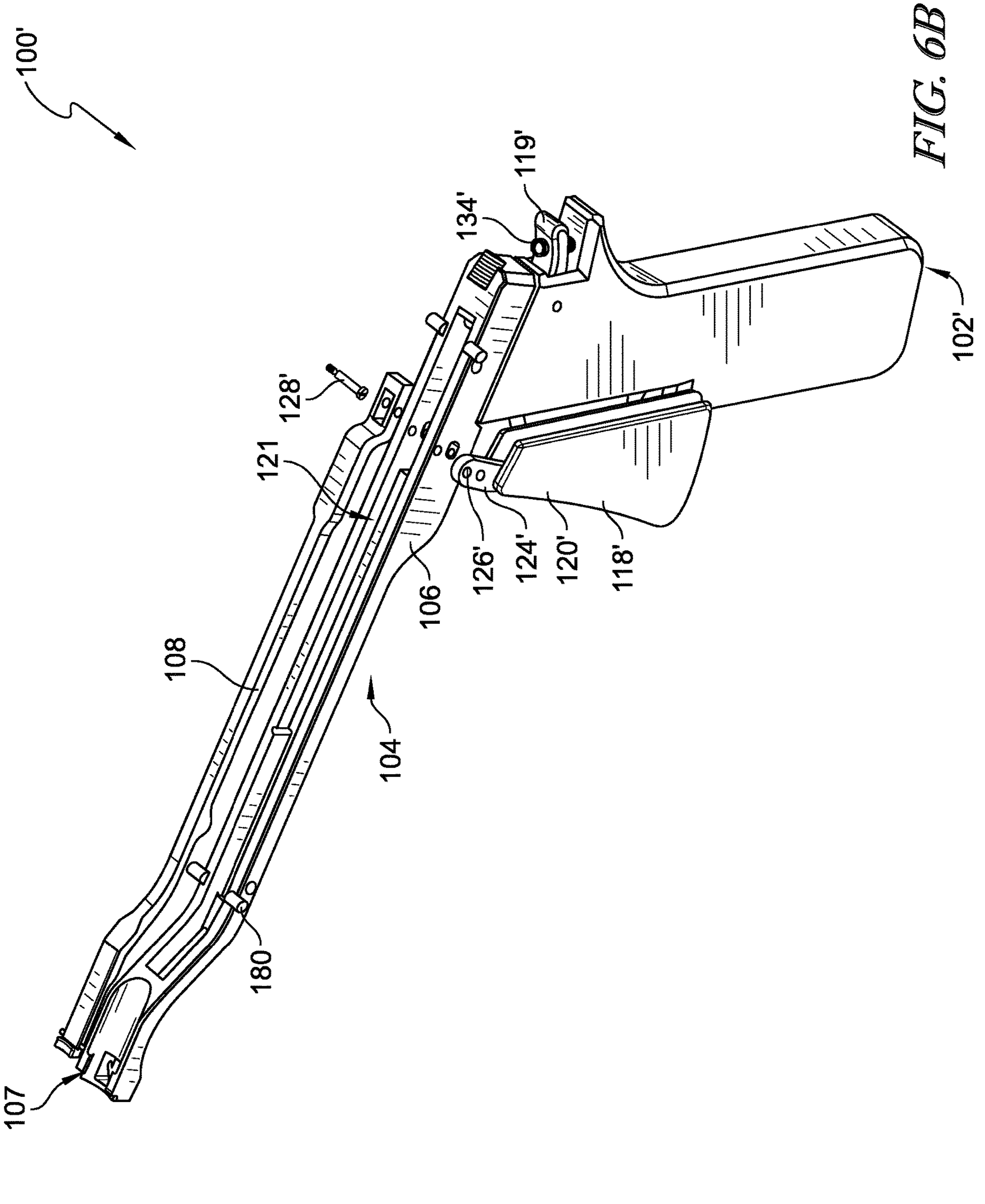
FIG. 6B is an exploded view of the instrument of FIG. 6A.
Figure 6C:
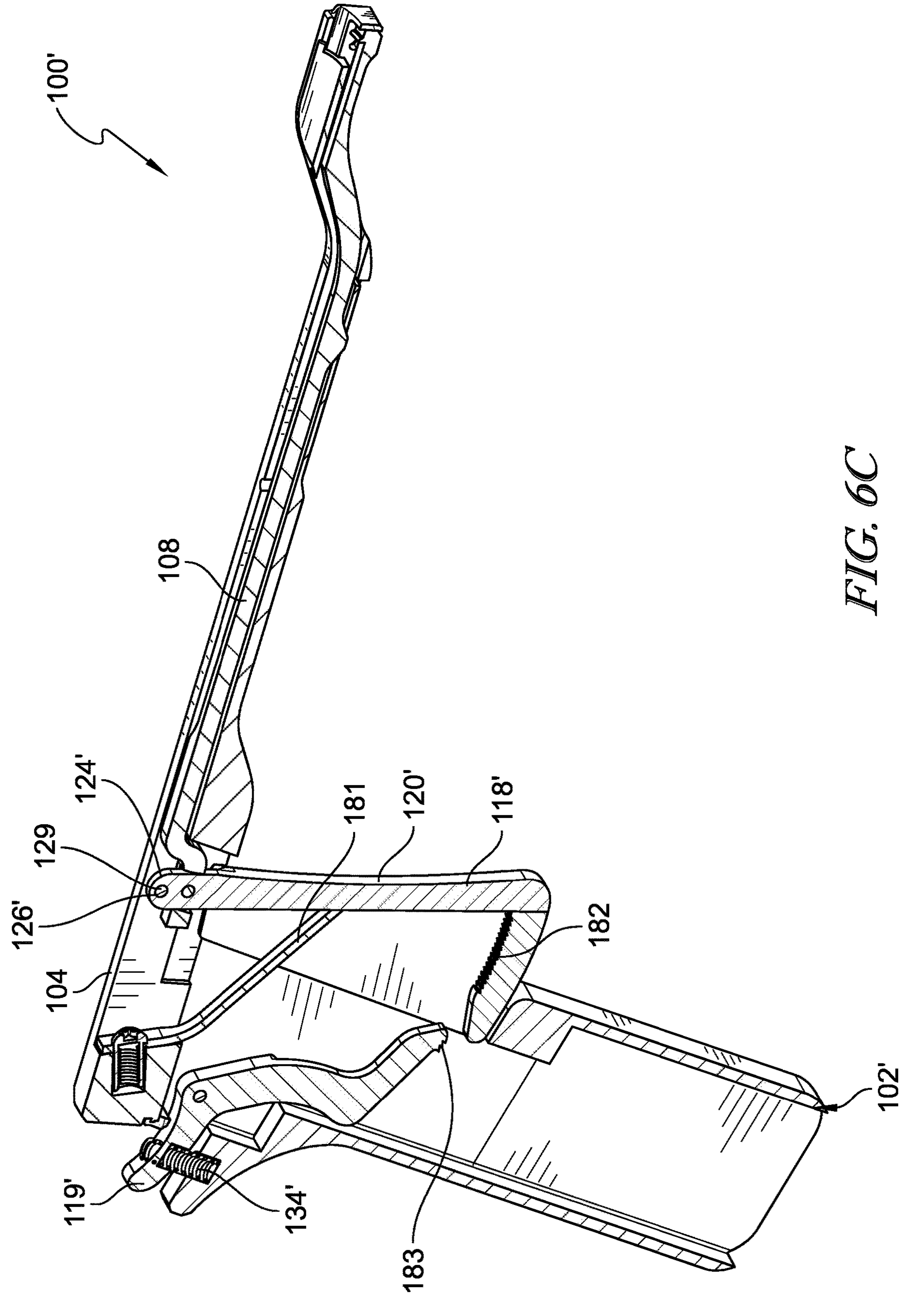
FIG. 6C is a side longitudinal cross-sectional view of the instrument of FIG. 6A.

As can be seen in the longitudinal cross-sectional view of FIG. 6C, the lock handle 118' can be pivotably coupled to the inserter portion 104 by a pin 129, and also pivotably coupled to the control shaft 108 such that actuation of the lock handle, e.g., by squeezing the lock handle into the handle 102', will draw the control shaft 108 proximally in a manner that can securely couple a connector 200 to the instrument 100'. A spring 181, such as a leaf spring, can impart a bias force to maintain the lock handle 118' in an extended state where the instrument 100' is in an unlocked configuration and ready to receive a connector 200. The lock handle 118' can include a ratchet 182 formed on an internal surface thereof that can interface with a pawl 183 that is part of the release button 119'. The release button 119' is biased to maintain the pawl 183 in connection with the ratchet 182 until a user depresses the release button 119' to overcome the bias force of the spring 134' and move the pawl 183 away from the ratchet 182. This also allows the spring 181 to return the lock handle 118' to its unlocked configuration.

Figure 7:
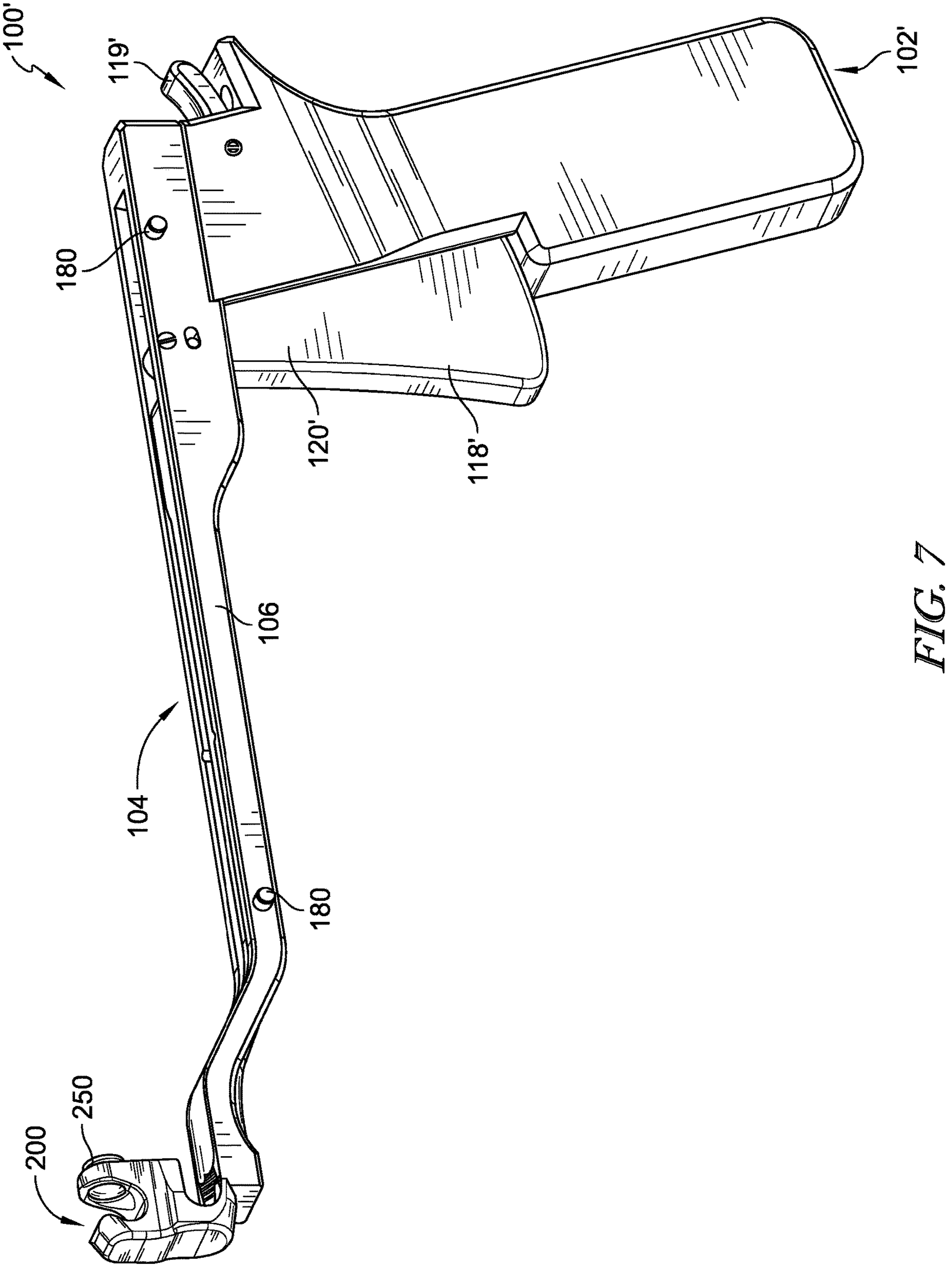
FIG. 7 is a perspective view of the inserter instrument of FIG. 6A coupled to the implant of FIG. 2A.
Figure 8A:
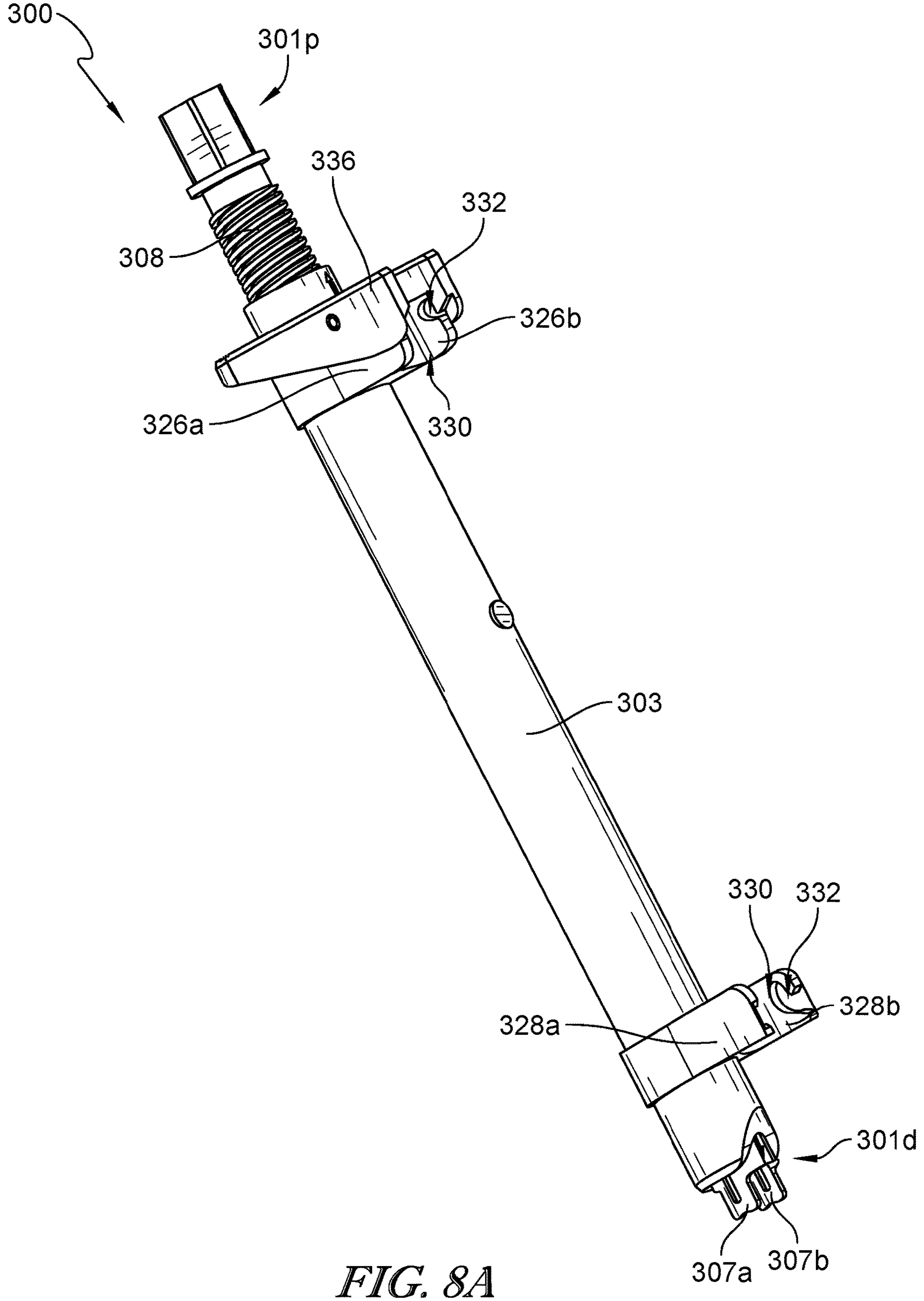
FIG. 8A is a perspective view of one embodiment of a reducer instrument that can be used as an auxiliary instrument with the inserter instrument of the present disclosure.
Figure 8B:
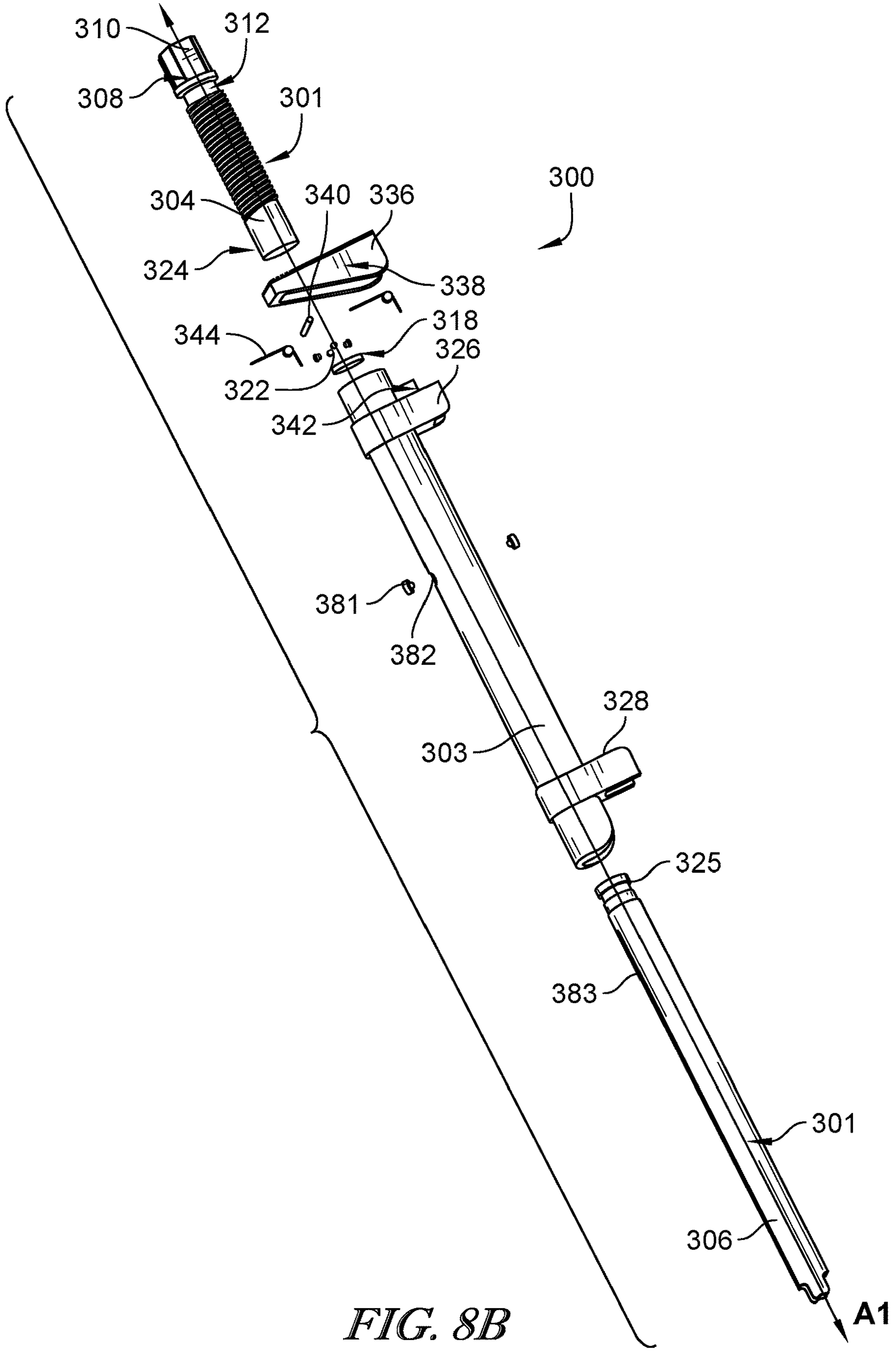
FIG. 8B is an exploded view of the reducer instrument of FIG. 8A.
Figure 8C:
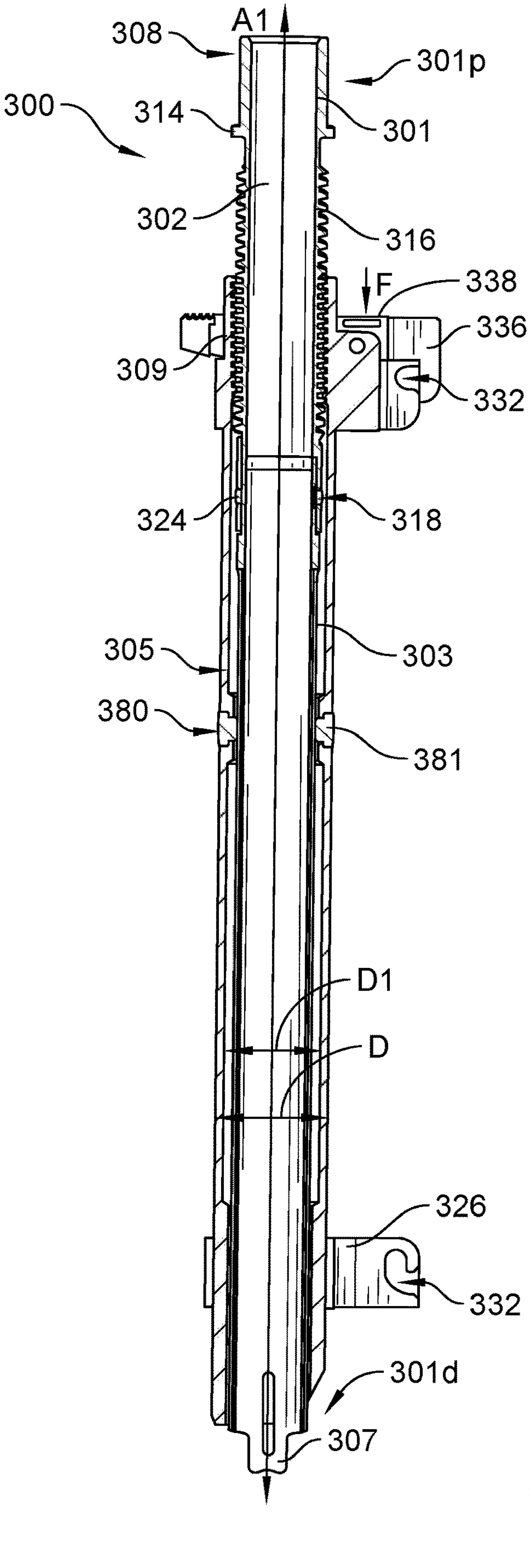
FIG. 8C is a side longitudinal cross-sectional view of the instrument of FIG. 8A.

The inserter portion 104 can include one or more attachment features extending therefrom for coupling the instrument 100 to one or more auxiliary instruments. As shown in FIG. 7, the attachment features can include pins 180 that extend from the body 106 that are configured to be coupled to auxiliary instruments. FIGS. 8A-8C illustrate one embodiment of a reducer instrument 300 that can be used with the inserter instruments of the present disclosure. As shown, the reducer instrument 300 can include a reducer shaft 301 disposed within a housing 303 that is configured to be coupled to the inserter instrument 100, as discussed in greater detail below.

The reducer shaft 301 can include a generally cylindrical shaft having a proximal end 301*p* and a distal end 301*d* with an inner lumen or working channel 302 passing therethrough. The reducer shaft 301 can have an outside diameter D1 that is smaller than the diameter D of a channel 305 formed in the housing 303 such that the reducer shaft 302 can be inserted through the channel 305. In operation, at least a portion of the reducer shaft 302 can rotate relative to the housing 303 about the axis A1 to advance the reducer shaft 302 distally relative to the instrument body and the connector 200 secured thereto, thereby urging a rod towards a rod seat of the connector 200. The reducer shaft 301 can include a proximal portion 304 configured to rotate relative to the housing 303 and a distal portion 306 configured to remain at a fixed rotational position relative to the housing 303. The fixed rotational position can be one in which opposed arms 307*a*, 307*b* of the distal portion 306 are aligned with the rod to reduce the rod into the connector 200. As noted above, the reducer shaft 301 can be cannulated or can define a working channel therethrough, e.g., to allow the reducer shaft 301 to be inserted over a guidewire or to allow instruments, implants, or other objects to be inserted through the reducer shaft. For example, the reducer shaft 301 can allow a set screw or other closure mechanism, and an instrument for applying the set screw or closure mechanism, to be passed through the lumen 302 to apply the set screw or closure mechanism to the connector.

The proximal portion 304 can include a drive interface 308 to facilitate application of torque or other forces to the reducer shaft 302, e.g., for advancing the reducer shaft 302 along corresponding threads 309 of the housing 303 during rod reduction. The drive interface 308 can have any geometry that facilitates application of torque or other forces to the reducer shaft 302, such as a hex drive 310 as shown. The drive interface 308 be received in or otherwise coupled to an instrument to impart a driving force onto the proximal portion 304.

The proximal portion 304 can include a flange or shoulder 314 to limit the degree to which the proximal portion 304 can be received within a counterpart drive interface of an instrument, as described further below. The proximal portion 304 can include an exterior thread 316 configured to mate with the threads 309 of the housing 303. The proximal portion 304 can include a coupling 318 for attaching the proximal portion 304 to the distal portion 306. The coupling 318 can be configured to attach the proximal and distal portions 304, 306 to prevent relative longitudinal translation therebetween while still allowing free rotation of the proximal portion 304 relative to the distal portion 306 about the axis A1. As shown, the coupling 318 can include a plurality of pins 322 that are received within openings 324 in the proximal portion and extend into a circumferential groove 325 formed in the distal portion to constrain the proximal and distal portions 304, 306 against relative translation while allowing for relative rotation.

A second coupling 380 can be provided to selectively prevent relative rotation between the distal portion 306 and the housing 303 while allowing for relative translation between these components. For example, one or more pins 381 can be received within openings 382 formed in the housing 303 and extend into a counterpart longitudinal groove 383 formed in the distal portion 306 to constrain the housing 303 and the distal portion 306 against relative rotation while allowing for relative translation.

As noted above, the distal portion 306 can include one or more arms 307*a*, 307*b* (collectively 307) extending distally therefrom. The arms 307 can be configured to contact and bear against a spinal rod to urge the rod distally as the reducer shaft 301 is translated distally within the housing 303. The distal contact surfaces of the arms 307 can be shaped to match a rod with which the reducer shaft 301 is to be used. For example, the arms 307 can include circular cut-outs having a diameter commensurate with the rod diameter. Though two arms 307*a*, 307*b* are shown, the reducer shaft 302 can include any number of rod-engaging arms.

As noted above and as shown in FIG. 8C, the outer housing 303 can include threads 309 that are configured to interface with the threads 316 to control movement of the reducer shaft 302 through the housing 303. The housing 303 can include one or more sets of arms extending therefrom for coupling the reducer instrument 300 with the inserter instrument 100. For example, as shown, the housing 3003 can include a first set of arms 326*a*, 326*b* (collectively 326) on a proximal end 303*p* of the housing and a second set of arms 328*a*, 328*b* (collectively 328) on a distal end 303*d* of the housing 303 configured to engage the inserter instrument 100 therebetween. Each pair of arms 326, 328 can define a recess 330 that is configured to receive a portion of the inserter instrument 100' therein. Inner-facing surfaces of arms 326, 328 can include a recessed track 332 to receive one of the pins 180 that extend from the elongate body 106 of the inserter instrument 100'. The recessed tracks 332 can be formed in the arms 326, 328 such that the pins 180 enter and slide in a direction towards the housing 303 to position the reducer instrument 300 relative to the inserter instrument 100.

A retaining lever 336 can be coupled to the housing 303 to toggle the reducer instrument 300 between an unlocked and a locked configuration. For example, the retaining lever 336 can pivot relative to the housing 303 to lock the pins 180 into the recessed tracks 332 to lock the reducer instrument 300 to the inserter instrument 100' in the locking configuration and release the pins 180 from the recessed tracks 332 to unlock the reducer instrument 300 from the inserter instrument 100. The retaining lever 336 can include a body 338 configured to be disposed around the housing 303. The retaining lever 336 can be coupled to the housing 330 by a pair of pins 340 received in corresponding openings 342 in the arms 326, 328. A bias element, e.g., a spring 344, can be disposed between the retaining lever 336 and the arms 326, 328 to exert a biasing force onto the retaining lever 336. The biasing force can maintain the lever 336 in a locked configuration that blocks an entrance to the tracks 332. In this manner, a user must actuate the lever 336 to clear the opening to the tracks 332 and allow coupling of the housing 303 to an inserter instrument 100'. This is in contrast to the lower arms 326, where the tracks 332 formed therein are always open. This facilitates a coupling sequence in which a user slides the lower pins of the inserter instrument 100' into the tracks 332 of the arms 326, then pivots the reducer instrument 300 such that the upper arms 328 move toward the inserter instrument and the upper pins thereof. The user then actuates the lever 336 to allow the upper pins to slide into the tracks 332 of the upper arms 328. Releasing the lever 336 with the pins disposed in the tracks 332 will prevent the pins from coming out of the tracks 332, thereby maintain the reducer instrument 300 in position relative to the inserter instrument 100'.

Figure 9:
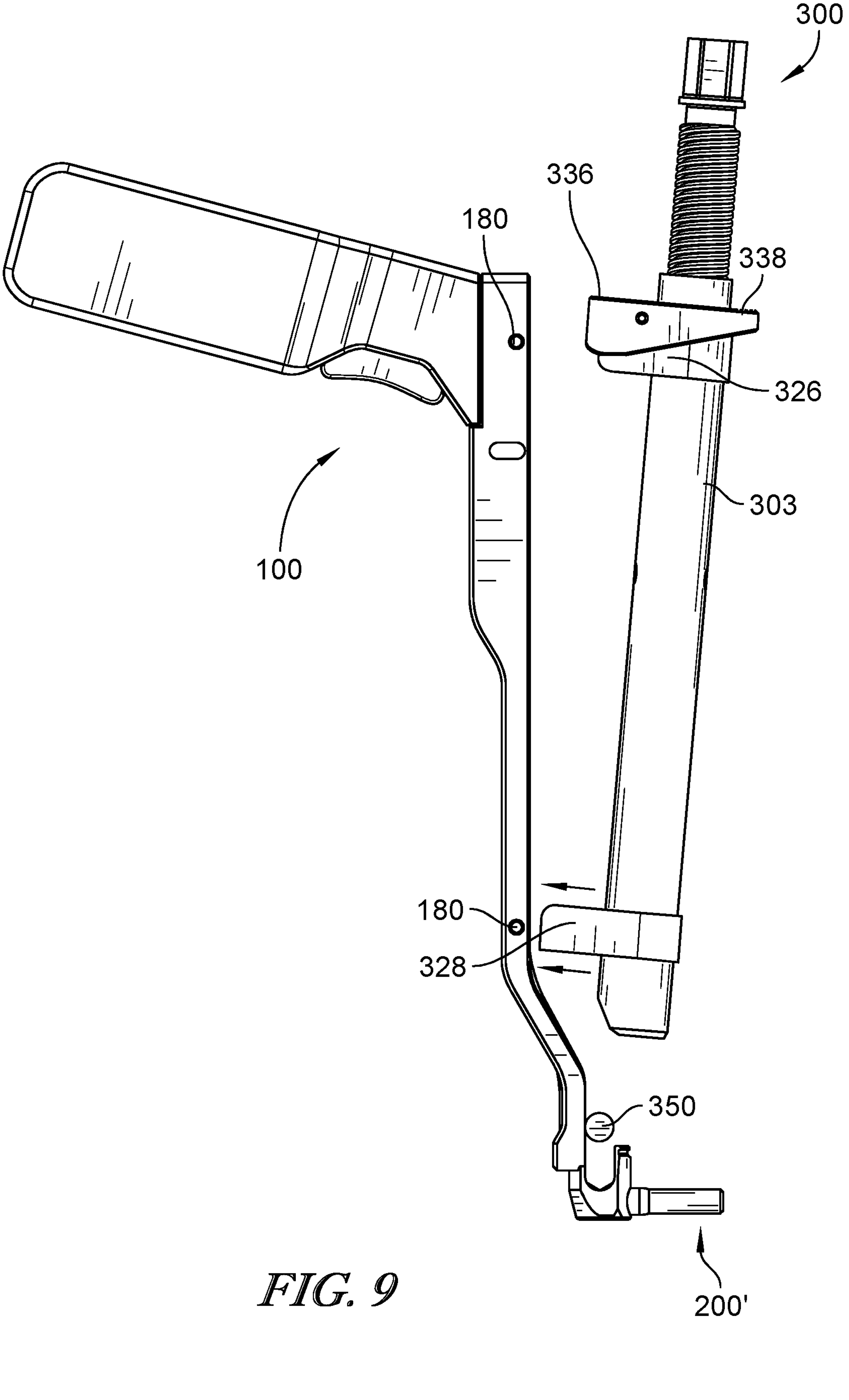
FIG. 9 is a side view of the reducer instrument of FIG. 8A being coupled to the inserter instrument of FIG. 6A.
Figure 10:
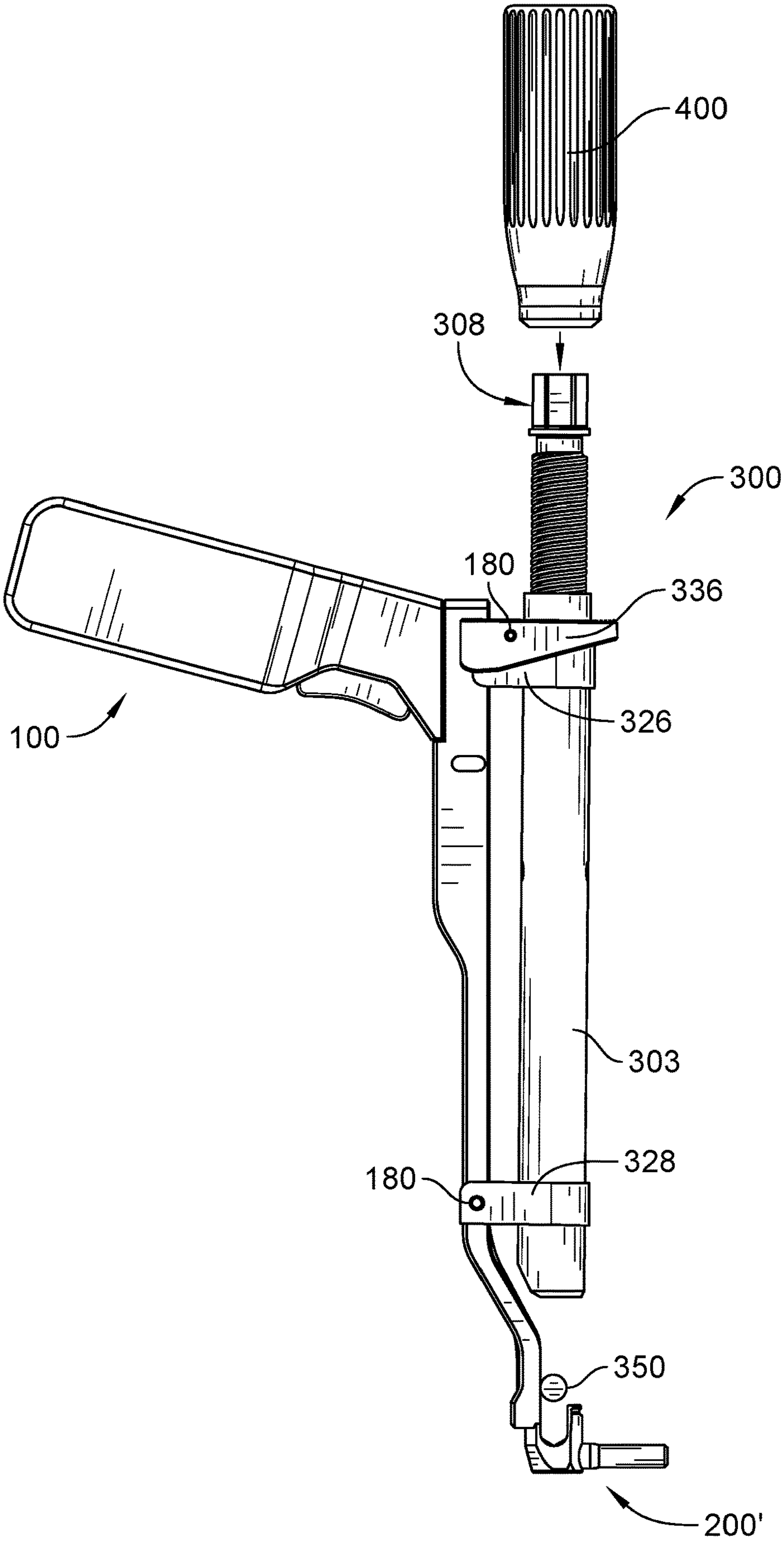
FIG. 10 is a side view of a drive handle being coupled to the assembly of FIG. 9.
Figure 11:
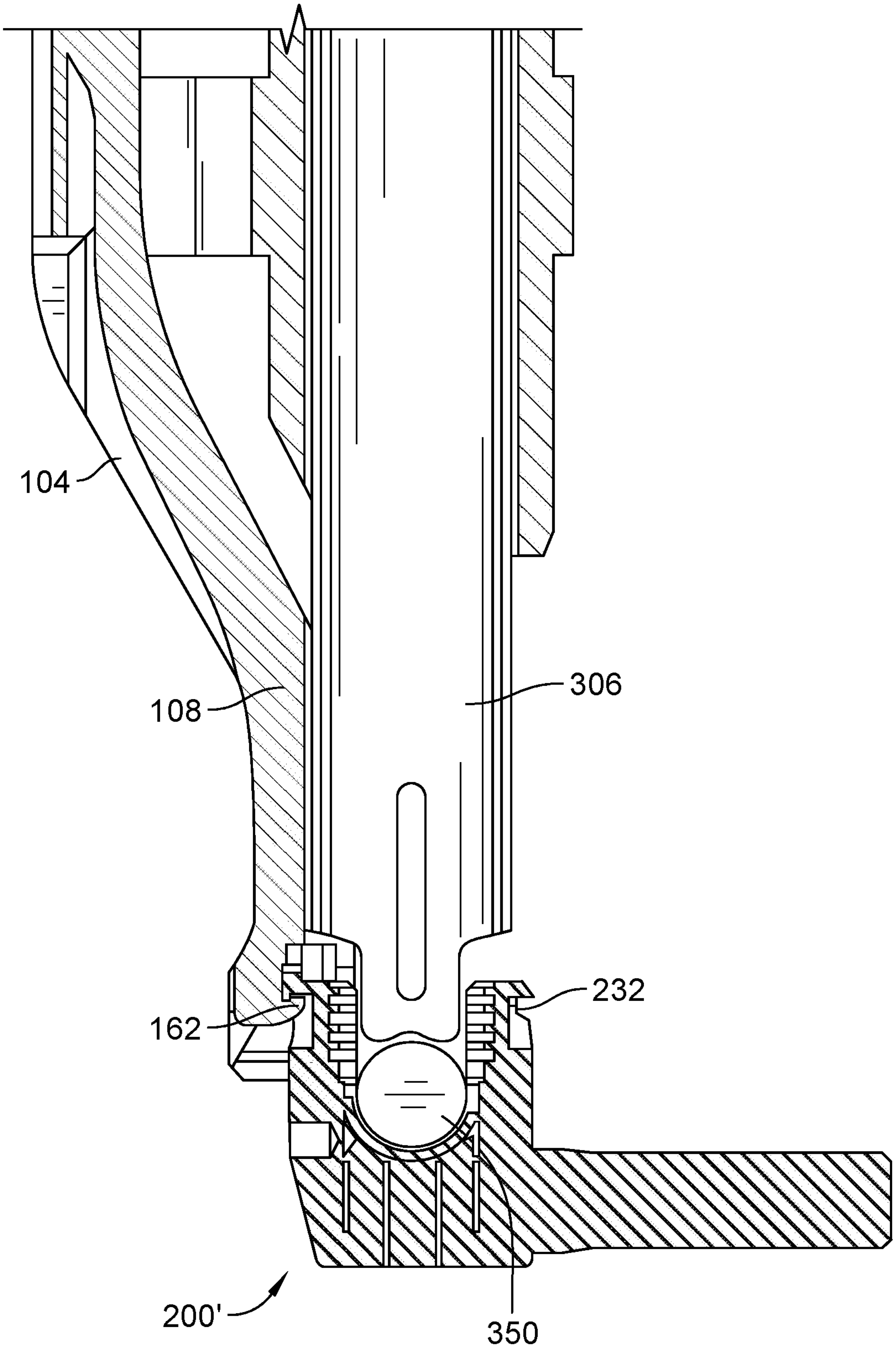
FIG. 11 is a detailed side longitudinal cross-sectional view of the assembly of FIG. 9 reducing a fixation element into a recess of an implant.

FIGS. 9-11 illustrate one embodiment of a coupling between the inserter instrument 100' and the reducer instrument 300. As shown, the arms 326, 328 that extend from the housing 303 of the reducer instrument 300 can receive the distal inserter portion 104 therebetween. The pins 180 can facilitate connection to the reducer instrument 300 by sliding along recessed tracks 332 in the arms 326, 328 until coupling is complete, as described above.

Once coupling is achieved, one or more instruments can be utilized with the reducer shaft 301 to reduce the spinal rod into the connector. As shown in FIGS. 10 and 11, a spinal rod 350 can be reduced into the connector 200' (a different type of connector is shown having a single open recess to receive a rod and a second rod component extending laterally therefrom but, as noted above, any variety of connectors or other implants can be utilized with the devices, systems, and methods disclosed herein) using the reducer instrument 300. Reduction can be performed using a drive handle 400 (or other driver, such as a powered driver, etc.) coupled to the drive interface 308 to reduce the spinal rod 350, while the inserter instrument 100' is docked to the connector 200' to provide counter-torque if needed. During reduction, the drive handle 400 can be rotated relative to the housing 303 to advance the reducer shaft 302 distally, which advances the distal portion 306 to contact the spinal rod 350 and urge the rod 350 into the recess of the connector 200'.

Figure 12:
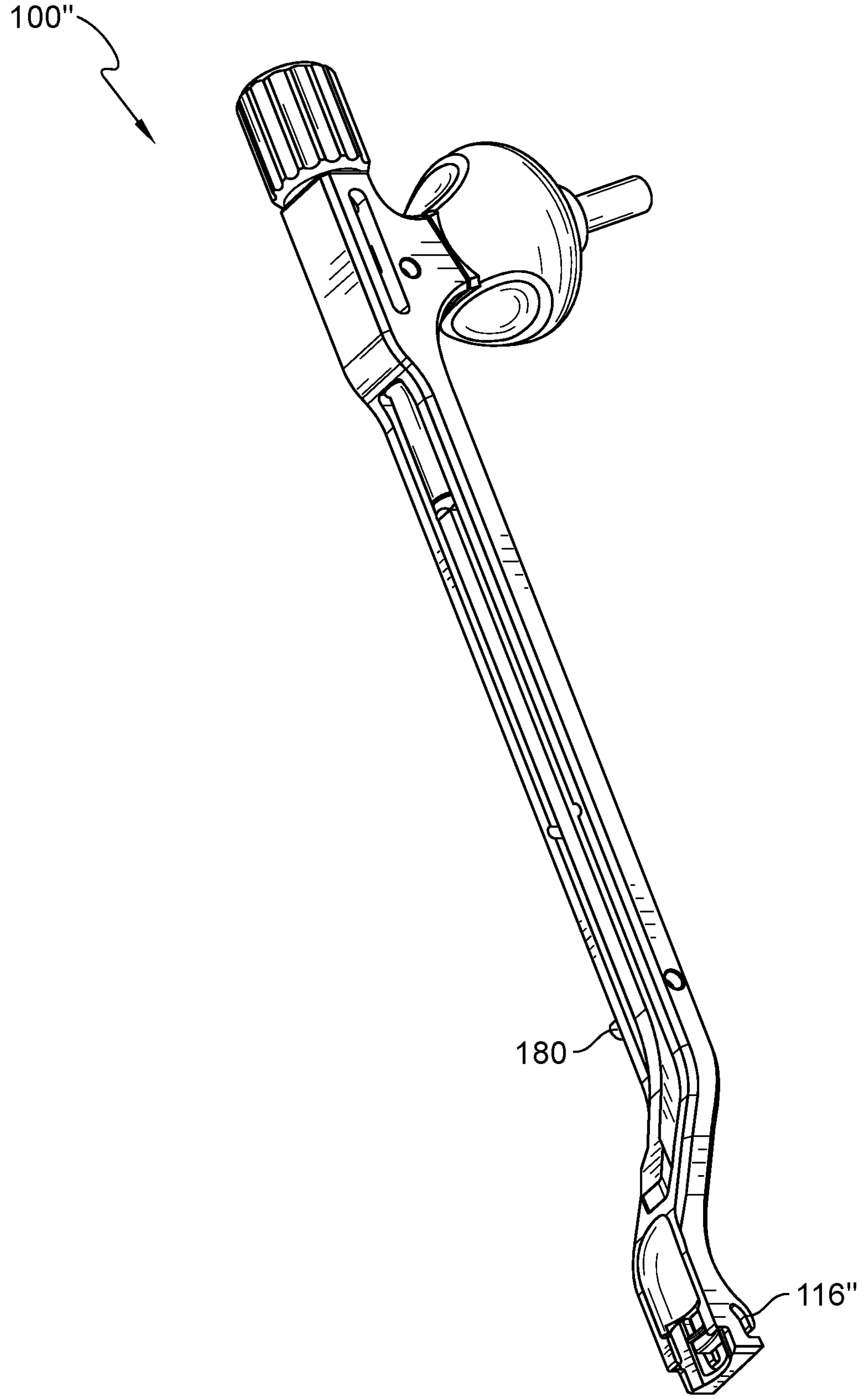
FIG. 12 is a perspective view of one embodiment of an inserter instrument.

The instruments 100, 3000 shown in FIGS. 1-5 are not shown with the pins 180 utilized to couple to secondary instruments, such as the reducer 300. Such features, however, are certainly contemplated for inclusion with the earlier-described inserter instruments 100, 3000. FIG. 12 illustrates one embodiment of an inserter instrument 100" that is similar to the inserter instruments of FIGS. 1-5 (e.g., utilizing a rotating knob actuator in favor of a trigger-style actuator) but includes pins 180 for coupling to secondary or auxiliary instrumentation, such as the reducer 300. The inserter instrument 100" also includes an alternative form of a track 116" that extends through a full thickness of the distal portion of the inserter portion 104 rather than only partially therethrough, such that the path of the track 116" can be seen from the side view of the instrument. This can be done for a variety of reasons, including allowing a deeper track that can accept a longer pin for greater strength, simplifying manufacturing processes (e.g., milling a track through a thickness of the distal portion of the instrument versus forming blind tracks on inner-facing surfaces thereof), etc.

Figure 13A:
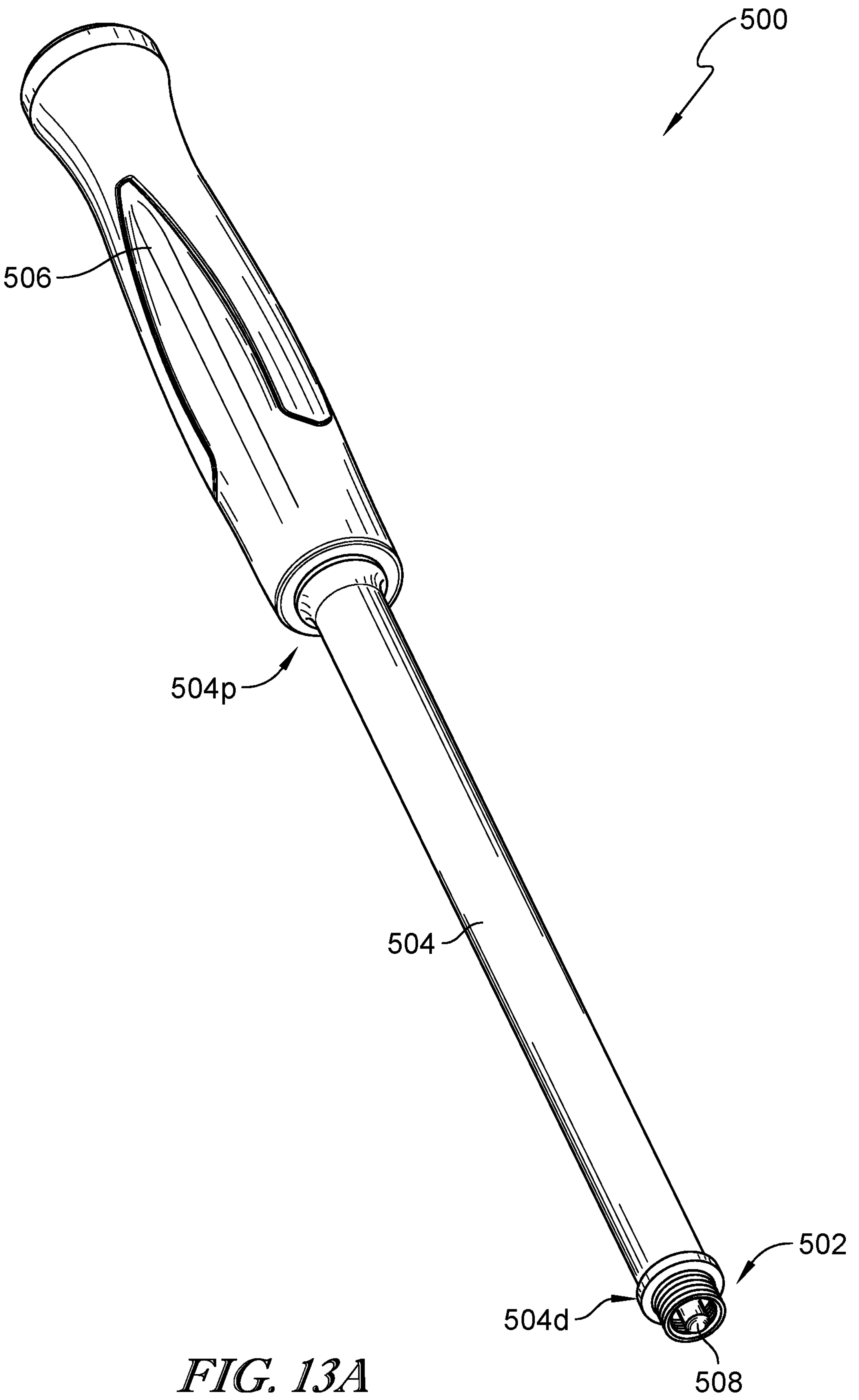
FIG. 13A is a perspective view of one embodiment of a holder instrument.
Figure 13B:
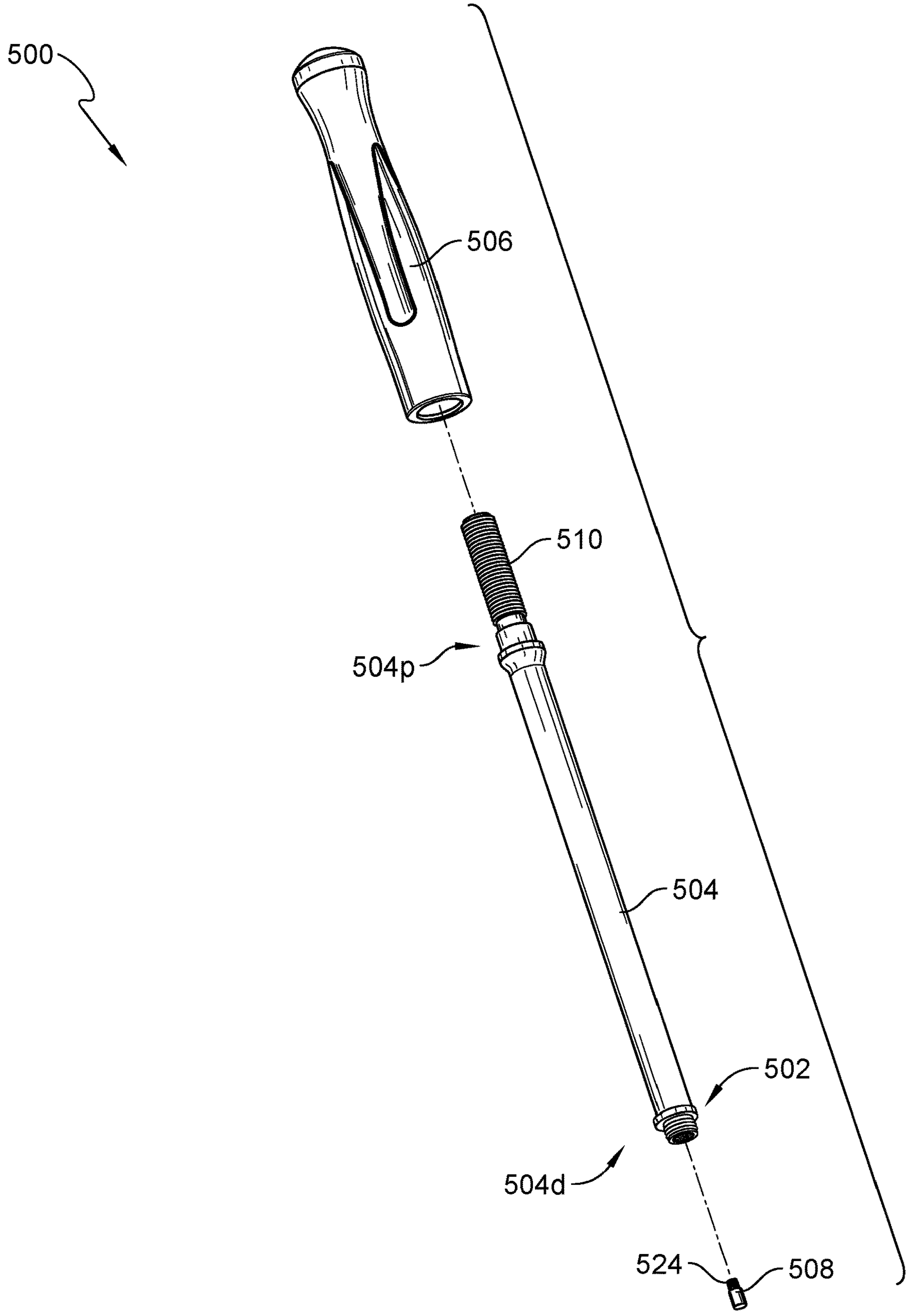
FIG. 13B is an exploded view of the holder instrument of FIG. 13A.

FIGS. 13A-13B illustrate one embodiment of a holder instrument 500 of the present disclosure. The holder instrument 500 can couple to the connector 200 or other implant to allow it to be introduced into the surgical site and attached to various hardware. The holder instrument 500 can include a distal engagement feature or surface 502 for coupling to the connector 200 to facilitate controlled insertion and/or manipulation of the connector 200 during a surgical procedure. The holder instrument 500 can include a longitudinal shaft 504 coupled to a proximal handle 506. The engagement features 502 can be disposed on a distal end **504*d* for coupling one or more connectors 200 to the handle 506. The engagement features 502 can include a centering pin 508 configured to be received within the connector 200. A proximal end 504*p* of the longitudinal shaft 504 can include a threaded surface 510 for engaging corresponding threads formed on an inner surface of the proximal handle 506** to couple the longitudinal shaft thereto.

Figure 14:
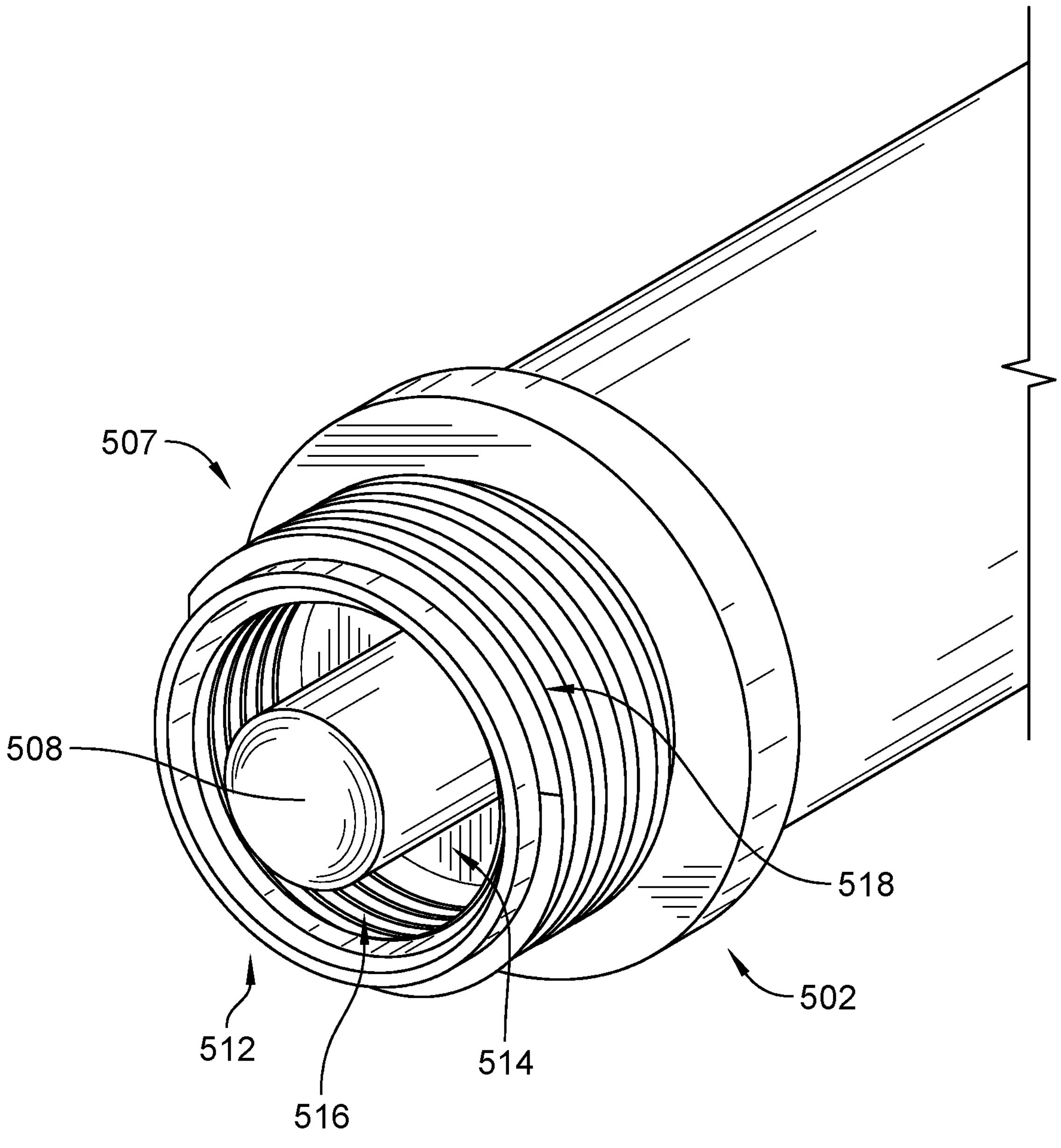
FIG. 14 is a detailed perspective view of a distal portion of the holder instrument of FIG. 13A.

FIG. 14 illustrates the engagement features 502 in greater detail. As shown, the engagement features 502 can include both male and female threads for coupling the holder instrument 500 to male and female threaded interfaces of a connector 200 though, as noted below, in some embodiments outer threads may not be present. For example, the engagement surface 502 can include a reduced diameter portion 507 that defines an opening 512 and associated recess 514 at the distal end of the longitudinal shaft 504 for receiving the centering pin 508 therein. The centering pin 508 can resemble a substantially cylindrical post that extends into a recess of the connector 200, e.g., a set screw drive feature recess 254 as shown in FIG. 2B. As shown, the opening 512 can surround the centering pin 508 such that an annular recess 514 is formed around the pin 508 that can receive a portion of a connector.

Figure 15:
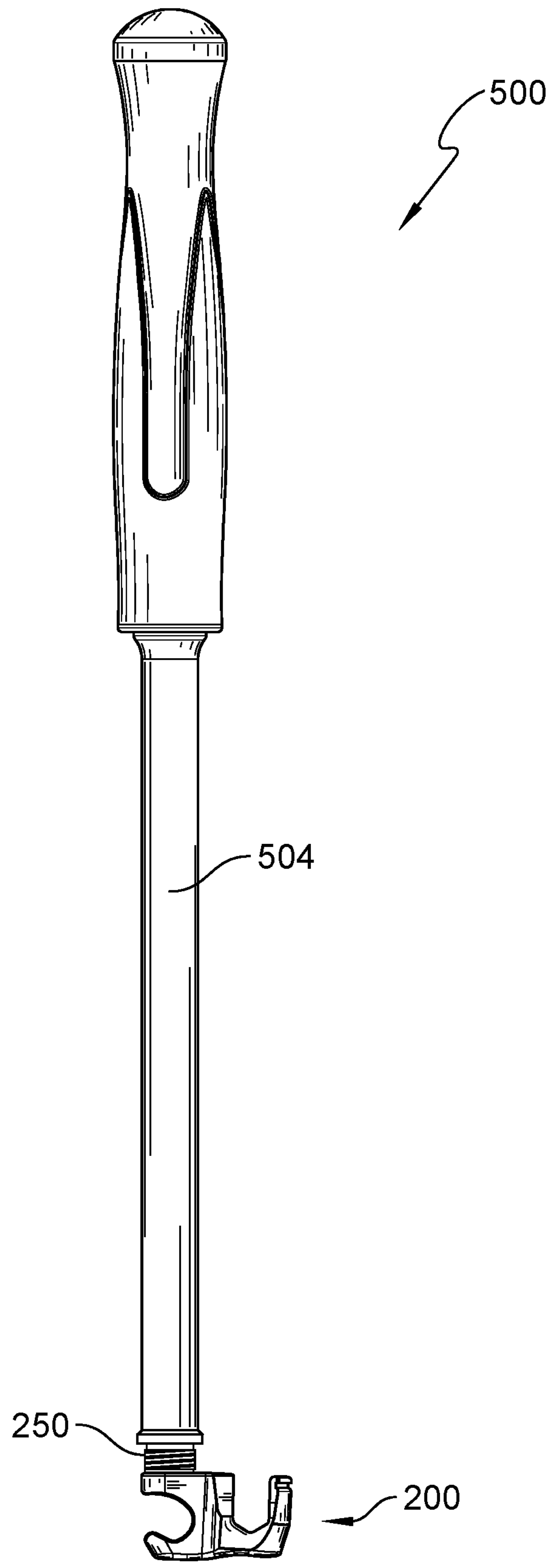
FIG. 15 is a side view of the holder instrument of FIG. 13A coupled with the connector of FIG. 2A via inner threads of the engagement feature.

The reduced diameter portion 507 can include one or more threaded surfaces for threadably disposing the engagement surface into, or into engagement with, the connector 200. In certain embodiments, such as the one illustrated in FIG. 14, multiple threaded surfaces can form a combination thread that can allow the holder instrument 500 to be used with connectors in a variety of manners. As shown, the engagement surface 502 can include an internal thread 516 and an external thread 518 disposed on the reduced diameter portion 507. The internal thread 516, or female thread, can extend along an inner surface of the reduced diameter portion 507 and can be utilized to couple with threads of a set screw 250 of the connector 200 that stand proud of a proximal surface of the connector. For example, as shown in FIG. 15, the engagement surface 502 can engage the set screw 250 (not visible, see FIGS. 2A-2B) of the connector 200 by inserting the centering pin 508 into an opening 254 of the set screw 250 with the internal thread 516 engaging the outer thread 252 of the set screw 250 to thread the holder instrument 250 thereon. In this configuration, the centering pin 508 can be received within the opening 254 of the set screw 250 with the set screw 250 being disposed in the annular recess 514 between the centering pin 508 and the inner thread 516. The arrangement of the centering pin and threaded coupling of the holder instrument 500 and set screw 250 can facilitate a rigid connection between the holder instrument 500 and the connector 200, thereby allowing a user to remotely manipulate the connector 200 using the holder instrument 500. Further, there can be a mismatch in the amount of force needed to rotate the set screw 250 relative to the connector 200 and the force needed to rotate the holder instrument 500 relative to the set screw 250, such that a user does not unintentionally rotate the set screw 250 relative to the connector 200 when coupling or decoupling the holder instrument 500 with the connector 200 via the set screw 250.

Figure 16:
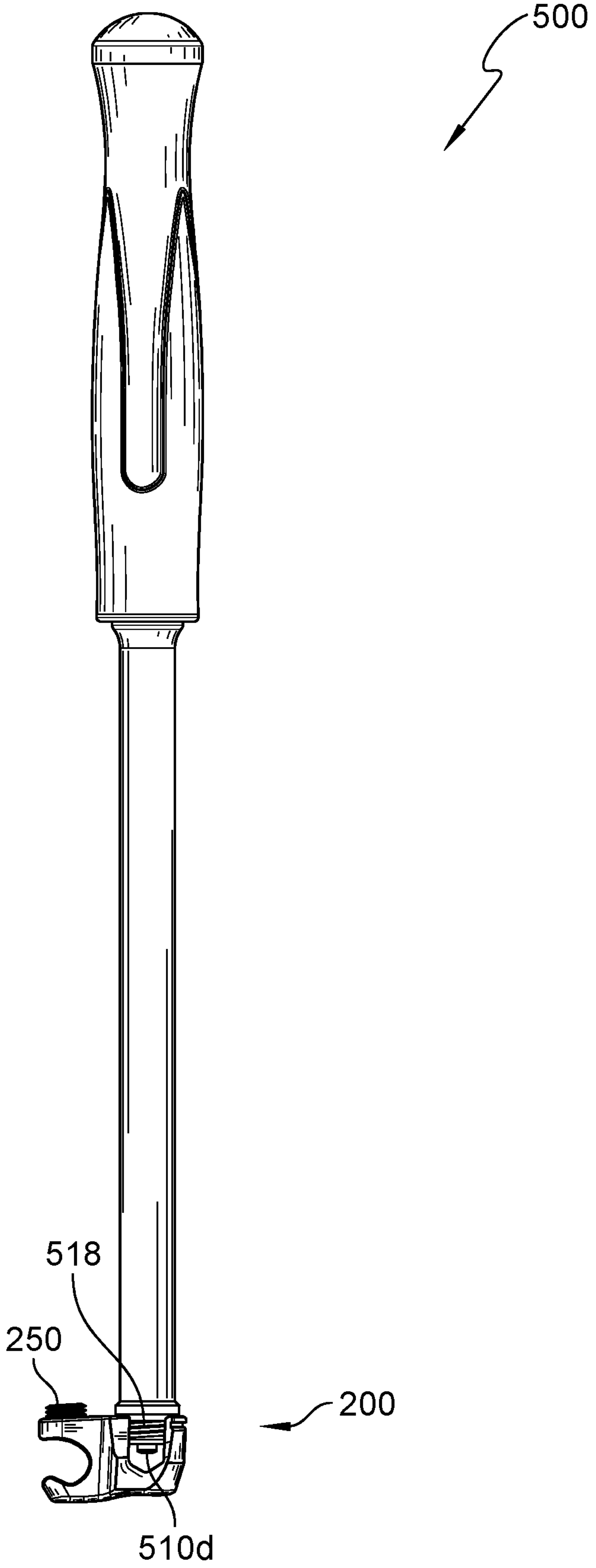
FIG. 16 is a side view of the holder instrument of FIG. 13A coupled with the connector of FIG. 2A via outer threads of the engagement feature.

The external thread 518, or male thread, can be used to thread into internal threads 240 of the connector 200. As shown in FIG. 16, the external threads 518 can be threaded into the corresponding internal threads 240 of the connector 200 or other implant to couple the holder instrument 500 thereto.

Figure 17:
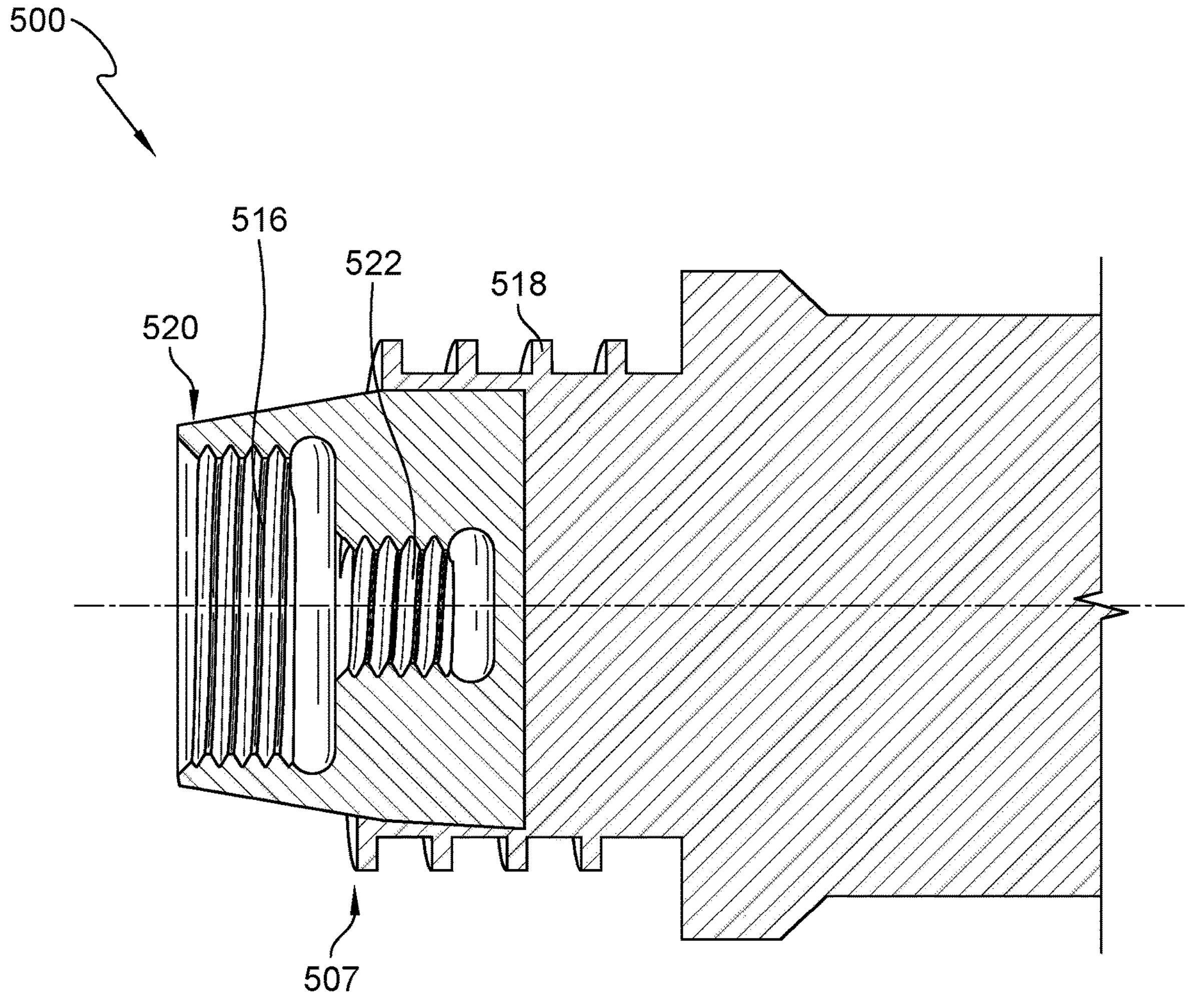
FIG. 17 is a side longitudinal cross-sectional view of one embodiment of an engagement feature of a holder instrument having an axial offset between inner threads and outer threads.

FIG. 17 illustrates an alternate embodiment of the engagement surfaces 502 of a holder instrument 500 that axially offsets the positions of the internal threads 516 and external threads 518 in order to increase the wall thickness of the instrument along a distal portion thereof. As shown in FIG. 17, the reduced diameter portion 507 of the holder instrument 500 can be extended beyond the distal end of the external threads 518 to create an extension 520 having a smooth outer wall. The internal threads 516 can be formed within the extension 520 such that the internal threads 516 proximally terminate at a position axially aligned with, or distal to, the distal-most external thread 518 (i.e., the proximal-most internal thread 516 is positioned at the same point as, or distal to, the distal-most external thread 518 when mapped along a longitudinal axis of the instrument 500). This can ensure there is no position along the length of the reduced diameter portion 507 where the internal threads 516 are axially aligned with the external threads 518 (i.e., they overlap one another when mapped along a longitudinal axis of the instrument 500). This can be desirable since positioning the internal and external threads in axial alignment with one another (i.e., they overlap one another when mapped along a longitudinal axis of the instrument 500) can reduce a thickness of material forming the reduced diameter portion that can increase a likelihood of breakage under load. Axially offsetting the internal and external threaded portions 516, 518, can allow for greater material wall thickness to be used throughout the reduced diameter portion 507.

Also shown in FIG. 17 is the smaller threaded bore 522 used to couple the centering pin 508 to the reduced diameter portion 507. For example, the centering pin 508 can include threads 524 (as shown in FIG. 13B) formed on a proximal end thereof that can be received in the threaded bore 522.

The outer wall of the extension 520 can have a tapered shape with a diameter that reduces moving toward a distal end of the extension in some embodiments. This shape can allow the extension 520 to extend deeper into a recess 202 of a connector or other implant as the holder instrument 500 is coupled thereto, e.g., by engaging the external threads 518 with the internal threads 240 of the connector 200. The taper can prevent interference as the holder instrument is advanced into the recess and, in some embodiments, the tapered outer surface of the extension 520 can abut a counterpart tapering internal surface of the connector recess 202, thereby strengthening the coupling between the components.

Figure 18:
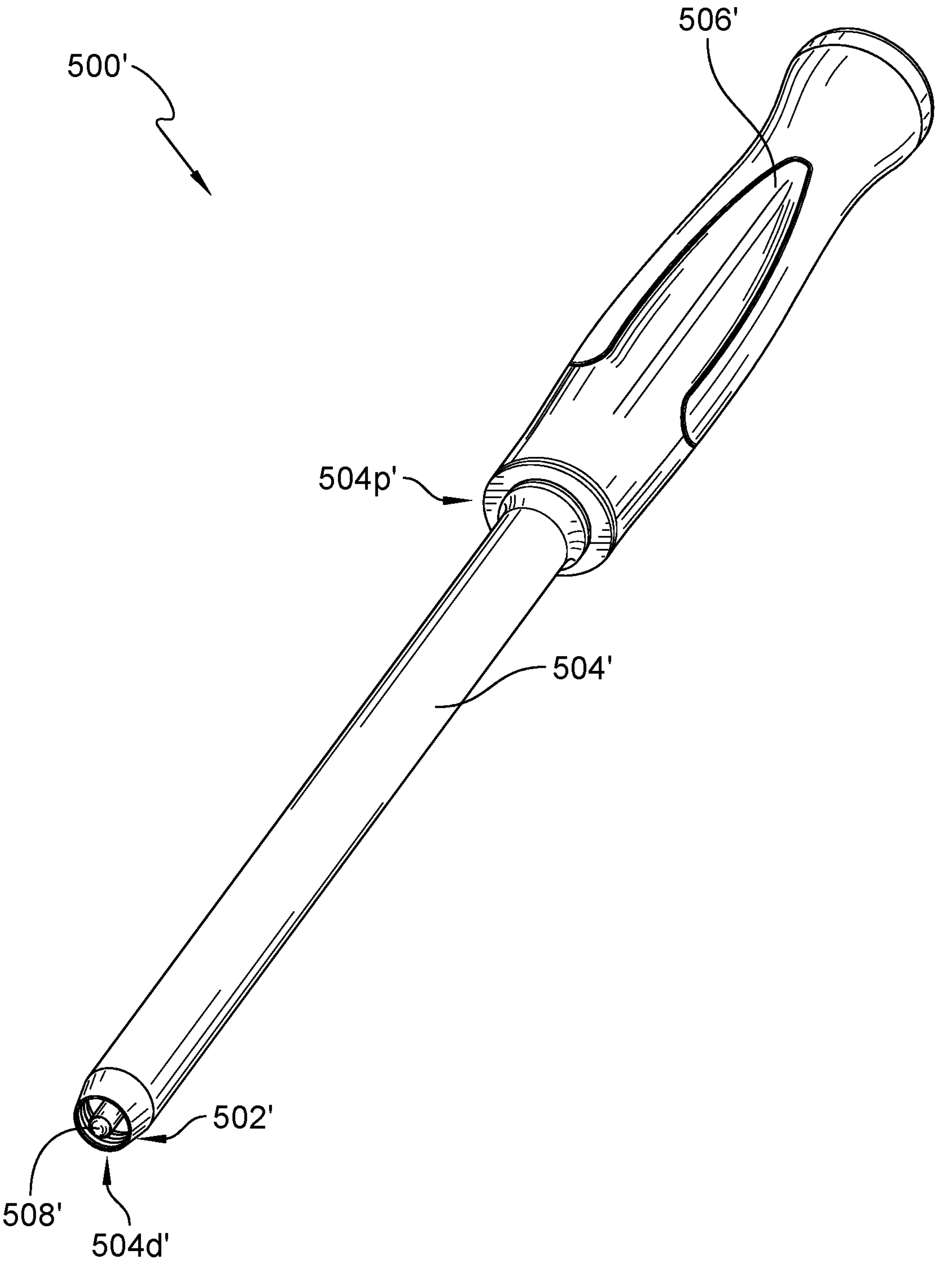
FIG. 18 is a perspective view of one embodiment of a holder instrument.

FIG. 18 illustrates another embodiment of a holder instrument 500' of the present disclosure. The holder instrument 500' can couple to the connector 200 or other implant to allow it to be introduced into the surgical site and coupled to other components, anatomy, etc. The holder instrument 500' can include a distal engagement feature or surface 502' for coupling to the connector 200 or other implant to facilitate controlled insertion and/or manipulation of the implant during a surgical procedure. The holder instrument 500' can include a longitudinal shaft 504' coupled to a proximal handle 506'. The engagement features 502' can be disposed on a distal end 504*d*' for coupling one or more connectors 200 or other implants to the handle 506'. The engagement features 502' can include a centering pin 508' configured to be received within the connector 200. In some embodiments, a proximal end 504*p*' of the longitudinal shaft 504' can include a threaded surface (not shown) for engaging corresponding threads formed on an inner surface of the proximal handle 506' to couple the longitudinal shaft thereto. In many respects, the holder instrument 500' can be similar to the holder instrument 500 described above, and detailed description is omitted to avoid repetition.

Figure 19:
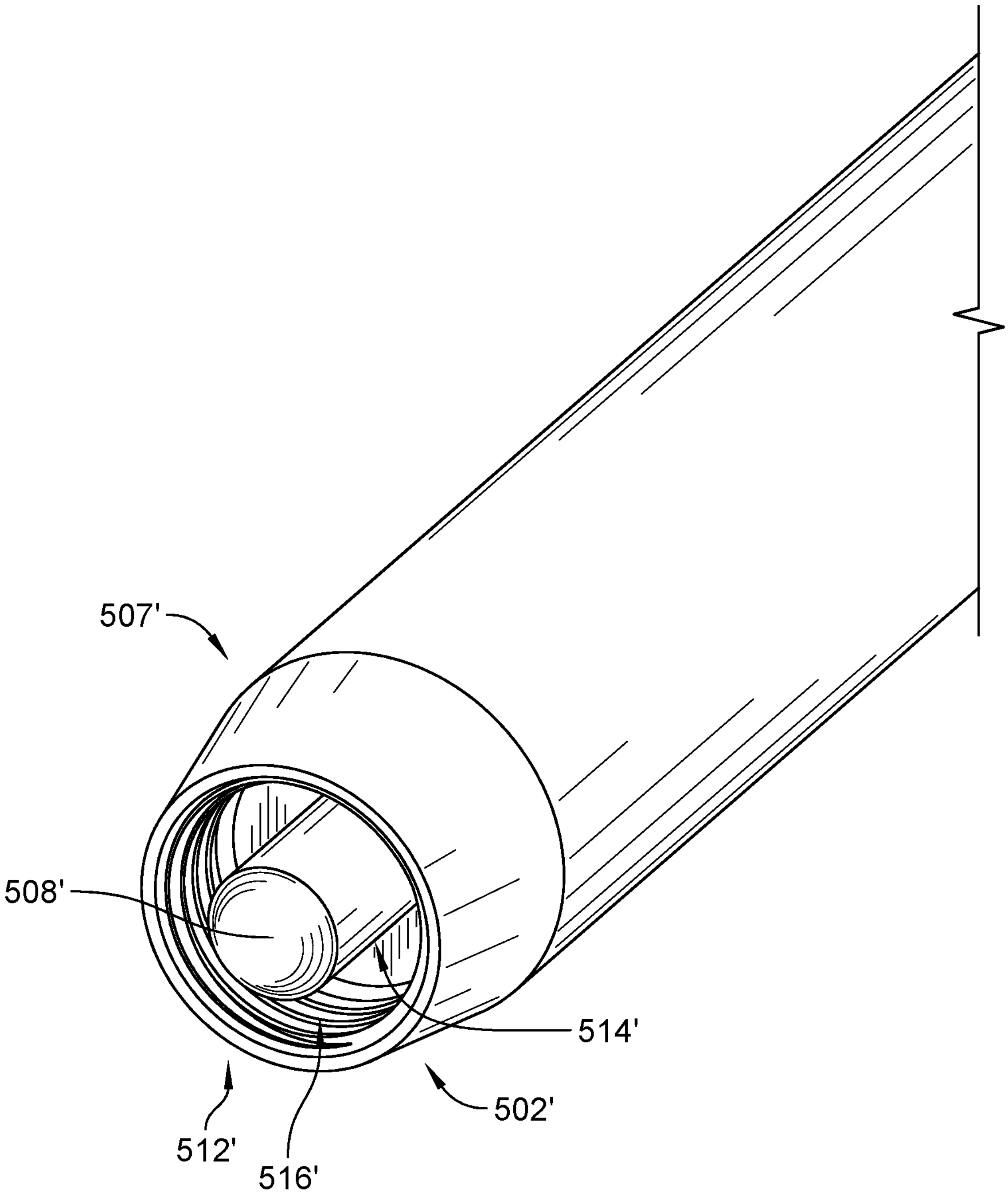
FIG. 19 is a detailed perspective view of a distal portion of the holder instrument of FIG. 18.

FIG. 19 illustrates the engagement features 502 in greater detail. As shown, the engagement features 502' can include threads for coupling the holder instrument 500' to threaded interfaces of a connector 200 or other implant. For example, the engagement surface 502' can include a reduced diameter portion 507' that defines an opening 512' at the distal end of the longitudinal shaft 504' for receiving the centering pin 508' therein. The centering pin 508' can resemble a substantially cylindrical post that extends into a recess of the connector 200, e.g., a set screw drive feature recess 254, as shown in FIG. 2B. As shown, the opening 512' can surround the centering pin 508' such that an annular recess 514' is formed around the pin 508' that can receive a portion of a connector.

The reduced diameter portion 507' can include a threaded surface for coupling the engagement surface with the connector 200 or other implant. As shown, the engagement surface 502' can include an internal thread 516' disposed on the reduced diameter portion 507'. As shown, the centering pin 508' can advance into a recess formed in the connector 200 or other implant and the internal thread 516' can interface with an external thread on the connector or another intermediate component. For example, the internal thread 516' can extend along an inner surface of the reduced diameter portion 507' and can be utilized to couple with, e.g., threads of a set screw 250 of the connector 200 that stand proud of a proximal surface of the connector. For example, the engagement feature 502' can engage the set screw 250 (see FIGS. 2A-2B) of the connector 200 by inserting the centering pin 508' into an opening 254 of the set screw 250 with the internal thread 516' engaging the outer thread 252 of the set screw 250 to thread the holder instrument 250 thereon. In this configuration, the centering pin 508' can be received within the opening 254 of the set screw 250 with the set screw 250 being disposed in the annular recess 514 between the centering pin 508 and the inner thread 516'. The arrangement of the centering pin and threaded coupling of the holder instrument 500' and set screw 250 can facilitate a rigid connection between the holder instrument 500' and the connector 200, thereby allowing a user to remotely manipulate the connector 200 using the holder instrument 500'. Further, there can be a mismatch in the amount of force needed to rotate the set screw 250 relative to the connector 200 and the force needed to rotate the holder instrument 500' relative to the set screw 250, such that a user does not unintentionally rotate the set screw 250 relative to the connector 200 when coupling or decoupling the holder instrument 500' with the connector 200 via the set screw 250.

Figure 20:
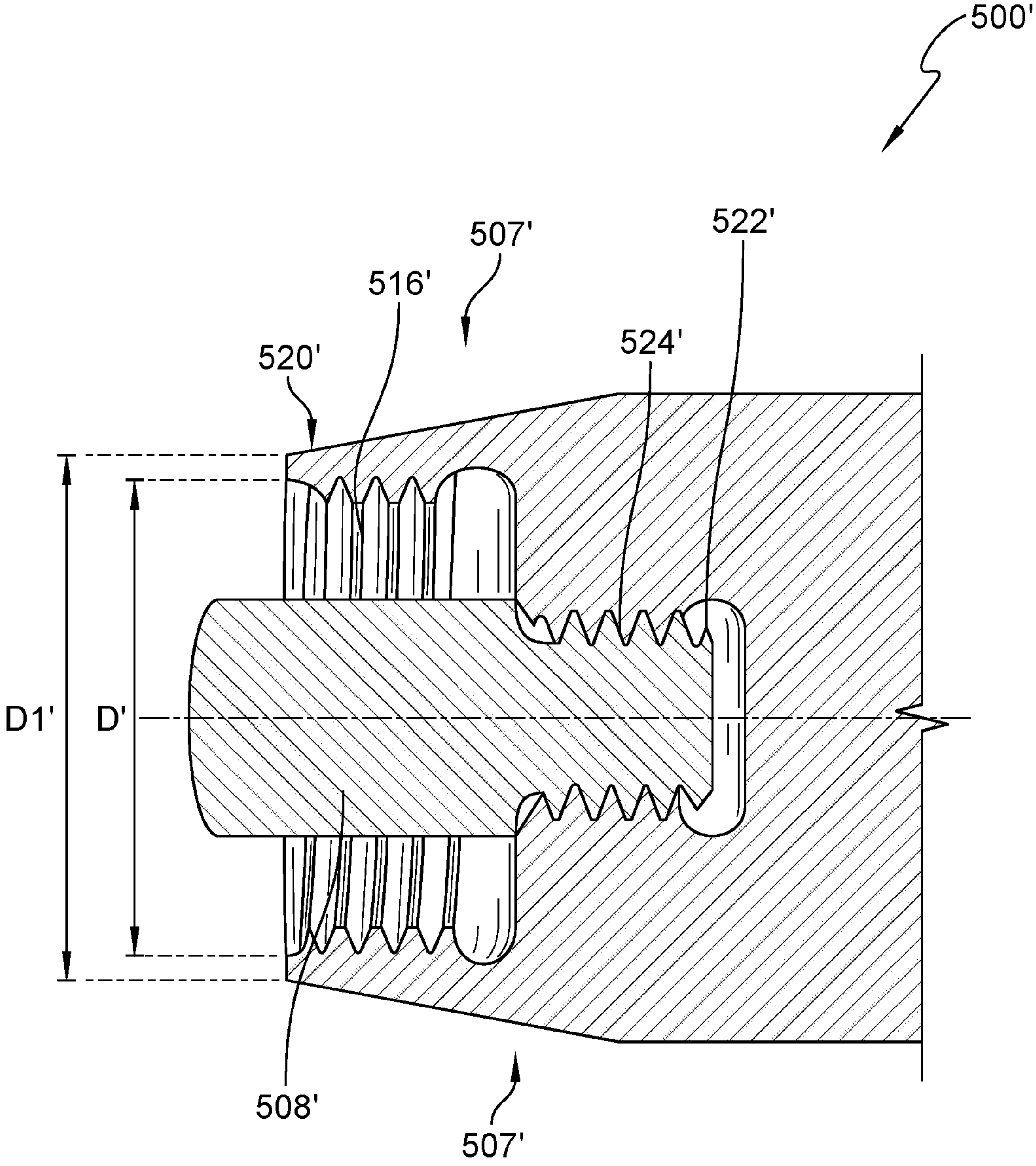
FIG. 20 is a side longitudinal cross-sectional view of an engagement feature of the holder instrument of FIG. 18.

FIG. 20 illustrates coupling of the centering pin 508' to the holder instrument 500'. As shown, the reduced diameter portion 507' of the holder instrument 500' can create an extension 520' having a smooth outer wall. The internal threads 516' can be formed within the extension 520' on an inner surface thereof without extending onto the outer wall. Utilizing only inner threads 516' can allow for maximizing a thickness of material forming the reduced diameter portion while also allowing for a distally-tapering outer diameter along the extension 520'. That is, a diameter D' of the internal threads 516' can be smaller than an outer diameter D1' of the reduced diameter portion 507'. In addition, the outer diameter D1' can decrease from a proximal end of the extension 520' to a distal end thereof. Also shown in FIG. 20 is the smaller threaded bore 522' used to couple the centering pin 508' to the instrument 500'. For example, the centering pin 508' can include threads 524' formed on a proximal end thereof that can be received in the threaded bore 522.

Figure 21:
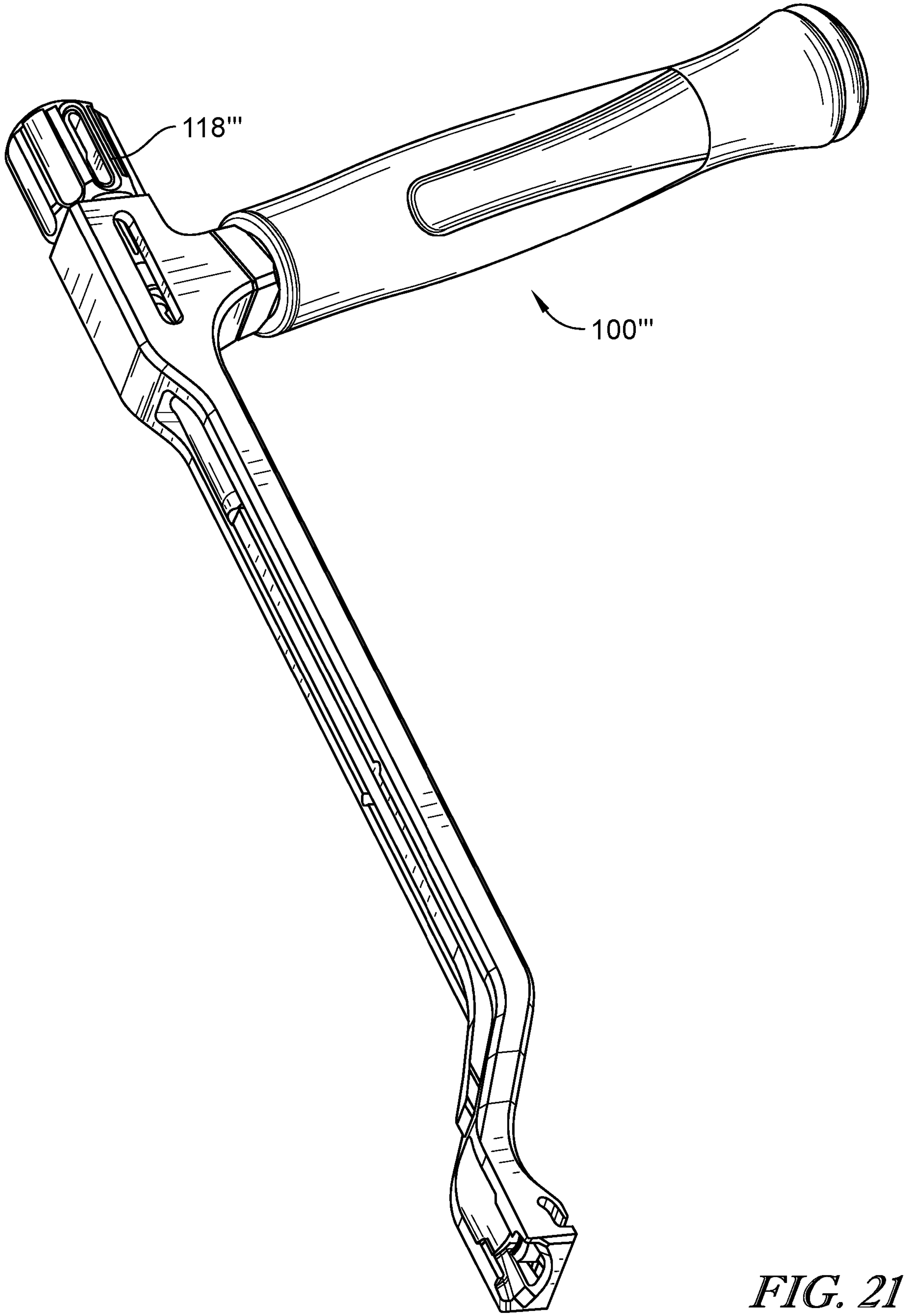
FIG. 21 is a perspective view of one embodiment of an inserter instrument.
Figure 22A:
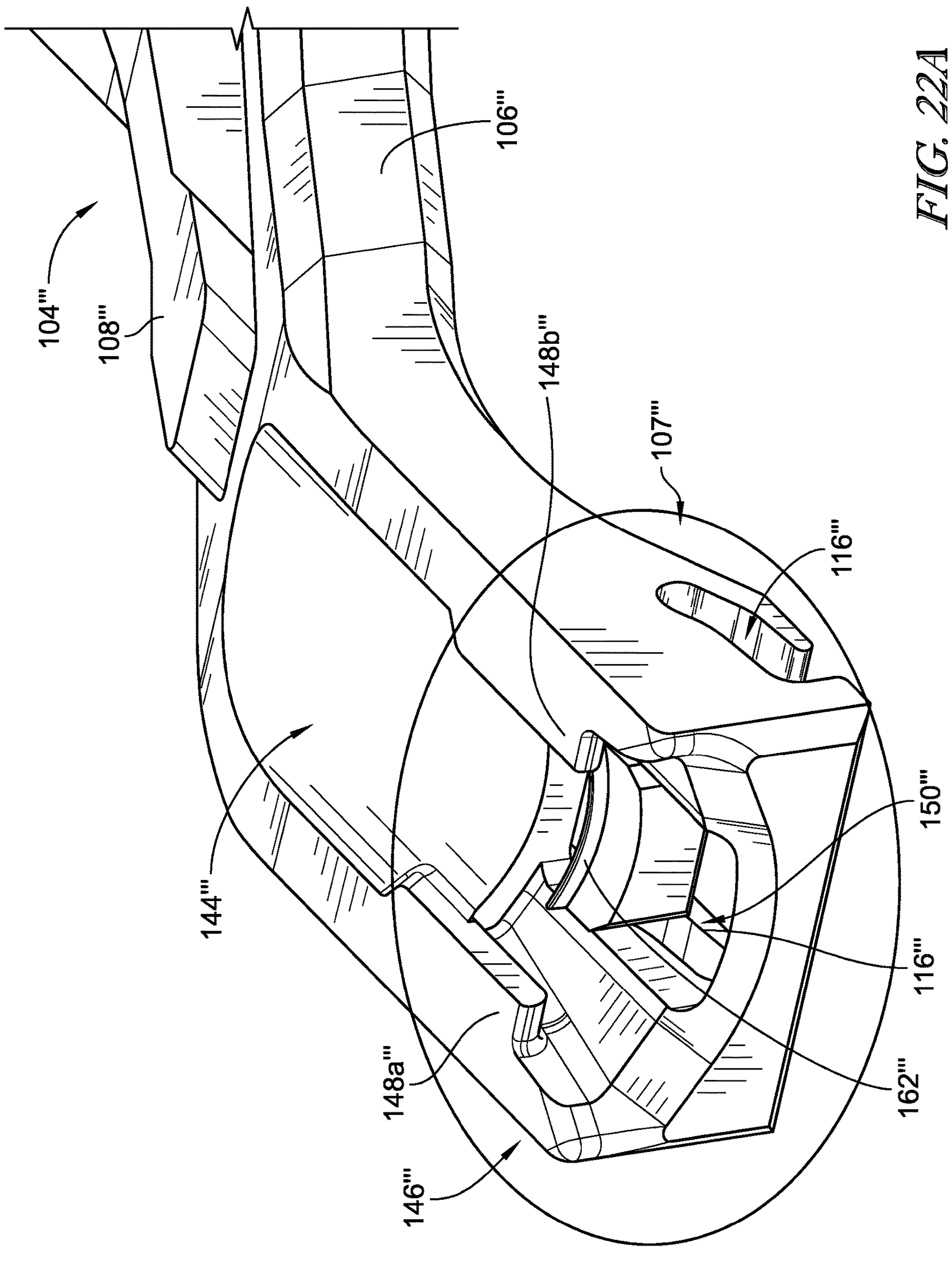
FIG. 22A is a detailed perspective view of a distal portion of the instrument of FIG. 21.
Figure 22B:
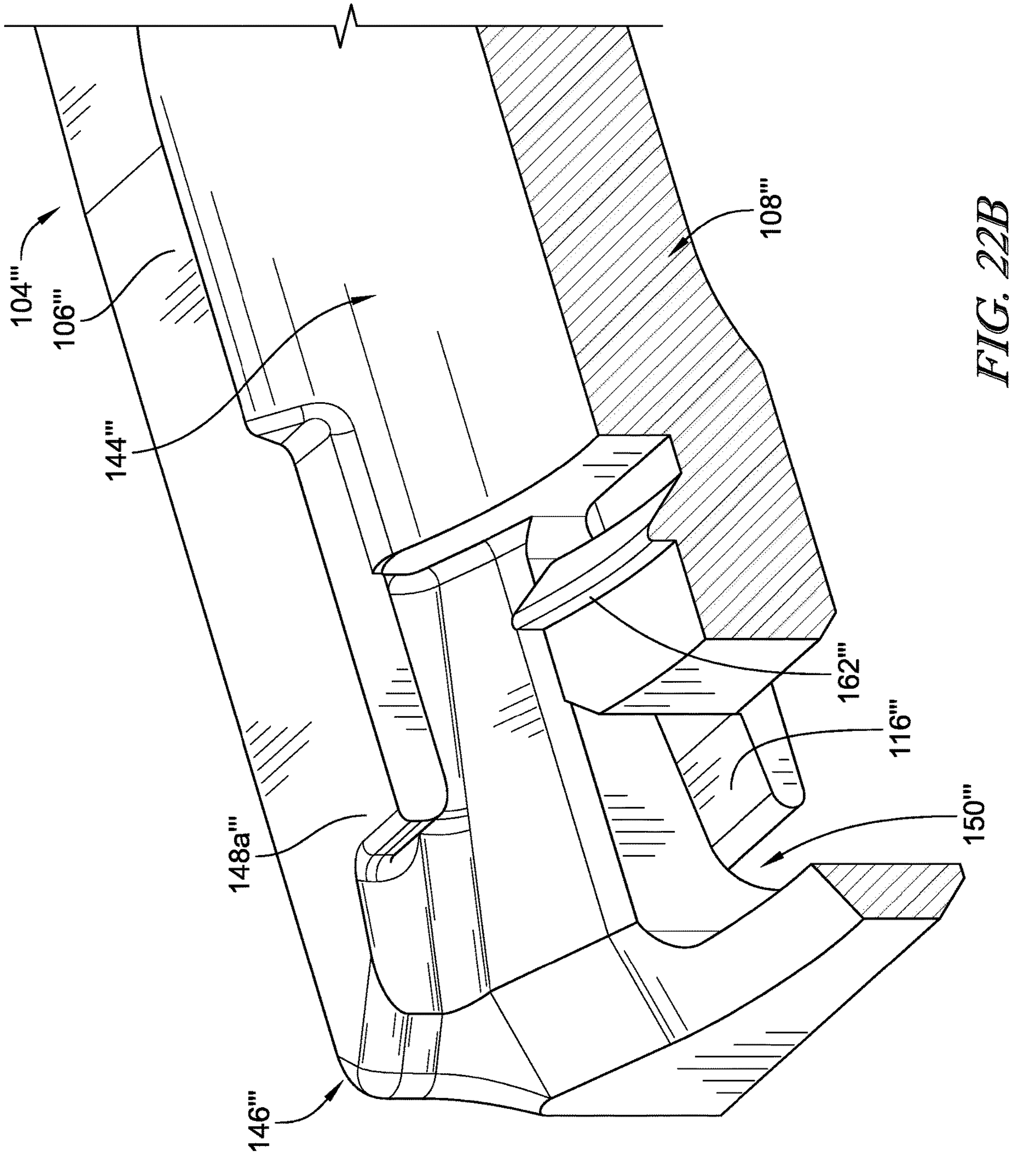
FIG. 22B is a detailed perspective longitudinal cross-sectional view of the distal portion of the instrument FIG. 21.

FIG. 21 illustrates another embodiment of an inserter instrument 100'''. The inserter instrument 100''' can be similar to the inserter instruments 100, 300 in many respects and, as a result, a detailed description of every feature is omitted for the sake of brevity. For example, the inserter instrument 100''' can be coupled to the unilateral portion 205 of the connector 200 or other implant such that the locking elements 107''' engage the unilateral portion 205 to secure the connector 200 or other implant in place. A distal portion of the inserter instrument 100''' that couples with the connector 200 is shown in detail in FIGS. 22A-22B. As discussed above, the inserter portion 104''' can include a recess 144''' that terminates with or includes the locking elements 107''' to couple with or uncouple from the connector 200. The elongate body 106''' of the inserter portion 104 can terminate in a forked instrument tip 146''' that can include a pair of parallel arms 148*a*''', 148*b*''' (collectively, 148'''). The spacing and dimensions of the arms 148''' can be configured to form an implant-receiving pocket 150''' between opposing faces of the arms 148'''. The pocket 150''' can be configured to accommodate a width and a depth of the unilateral portion 205 of the connector 200 or other implant.

The locking elements 107''' can include a retractable hook or clasp 162''' formed along a distal portion of the control shaft 108''' and disposed between the opposing faces of the arms 148''' at or adjacent to the back of the pocket 150'''. The hook 162''' can be configured to interface with the groove or notch 232 formed on the connector 200. The retractable hook 162''' can be configured to move proximally relative to the inserter portion 104''' and laterally toward the connector (e.g., upward and inward) as it moves from an unlocked configuration to a locked configuration in which the hook 162''' is disposed within the groove 232 of the connector 200. The retractable hook 162''' can be configured to move distally relative to the inserter portion 104 and laterally away from the connector (e.g., downward and outward) as it moves from a locked configuration to an unlocked configuration where the connector can be separated from the instrument.

The recess 144''' can be wider than that of recess 144 to provide a more robust lead-in surface into the locking elements 107''' of the inserter portion 104'''. Moreover, the locking elements 107''' can also be wider (e.g., extend further from the lateral sides of the elongate body 106''') than the locking elements 107 to increase robustness of the inserter instrument 100'''. For example, once the inserter instrument 100''' is locked to the implant, e.g., unilateral portion 250 of connector 200, the distal portion of the inserter portion 104''' can experience various forces during controlled insertion, manipulation, and/or counter torqueing of the implant during a surgical procedure. Widening the distal portion of the instrument, including the locking elements 107''', can help the instrument better handle these various forces without unwanted movement, deflection, etc. In some embodiments, transitions between larger and smaller connector capture openings can be gradual or smooth to prevent the connector from binding against a more abrupt transition (e.g., a step or a small-diameter curved transition).

The elongate body 106''' can include a track 116''' that extends through a full thickness of the distal portion of the inserter portion 104''' such that the path of the track 116''' can be seen from the side view of the instrument. As noted above with regard to FIG. 12 and the inserter 100'', this track configuration can be utilized to maximize a length of a pin or protrusion formed on the control shaft 108''' that rides within the track, to simplify manufacturing processes, etc. Further, and as noted above with regard to the track 116, the track 116''' can be ramped or angled relative to a longitudinal axis of the inserter portion 104''' such that a distal portion of the control shaft 108''' that includes the hook 162''' can be made to move in a second direction as it translates distally and proximally relative to the inserter portion.

Various devices and methods disclosed herein can be used in minimally-invasive surgery and/or open surgery. While various devices and methods disclosed herein are generally described in the context of surgery on a human patient, the methods and devices disclosed herein can be used in any of a variety of surgical procedures with any human or animal subject, or in non-surgical procedures.

Various devices disclosed herein can be constructed from any of a variety of known materials. Example materials include those which are suitable for use in surgical applications, including metals such as stainless steel, titanium, nickel, cobalt-chromium, or alloys and combinations thereof, polymers such as PEEK, ceramics, carbon fiber, and so forth. Further, various methods of manufacturing can be utilized, including 3D printing or other additive manufacturing techniques, as well as more conventional manufacturing techniques, including molding, stamping, casting, machining, etc.

Various devices or components disclosed herein can be designed to be disposed of after a single use, or they can be designed to be used multiple times. In either case, however, various devices or components can be reconditioned for reuse after at least one use. Reconditioning can include any combination of the steps of disassembly, followed by cleaning or replacement of particular pieces, and subsequent reassembly. In particular, a device or component can be disassembled, and any number of the particular pieces or parts thereof can be selectively replaced or removed in any combination. Upon cleaning and/or replacement of particular parts, the device or component can be reassembled for subsequent use either at a reconditioning facility, or by a surgical team immediately prior to a surgical procedure. Reconditioning of a device or component can utilize a variety of techniques for disassembly, cleaning/replacement, and reassembly. Use of such techniques, and the resulting reconditioned device or component, are within the scope of the present disclosure.

Various devices or components described herein can be processed before use in a surgical procedure. For example, a new or used device or component can be obtained and, if necessary, cleaned. The device or component can be sterilized. In one sterilization technique, the device or component can be placed in a closed and sealed container, such as a plastic or TYVEK bag. The container and its contents can be placed in a field of radiation that can penetrate the container, such as gamma radiation, x-rays, or high-energy electrons. The radiation can kill bacteria on the device or component and in the container. The sterilized device or component can be stored in the sterile container. The sealed container can keep the device or component sterile until it is opened in the medical facility. Other forms of sterilization are also possible, including beta or other forms of radiation, ethylene oxide, steam, or a liquid bath (e.g., cold soak). Certain forms of sterilization may be better suited to use with different devices or components, or portions thereof, due to the materials utilized, the presence of electrical components, etc.

In this disclosure, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B," "one or more of A and B," and "A and/or B" are each intended to mean "A alone, B alone, or A and B together." A similar interpretation is also intended for lists including three or more items. For example, the phrases "at least one of A, B, and C," "one or more of A, B, and C," and "A, B, and/or C" are each intended to mean "A alone, B alone, C alone, A and B together, A and C together, B and C together, or A and B and C together." In addition, use of the term "based on," is intended to mean, "based at least in part on," such that an un-recited feature or element is also permissible.

Further features and advantages based on the above-described embodiments are possible and within the scope of the present disclosure. Accordingly, the disclosure is not to be limited by what has been particularly shown and described. All publications and references cited herein are expressly incorporated herein by reference in their entirety, except for any definitions, subject matter disclaimers, or disavowals, and except to the extent that the incorporated material is inconsistent with the express disclosure herein, in which case the language in this disclosure controls.

Examples of the above-described embodiments can include the following:

1. A surgical instrument comprising:
   - a proximal handle;
   - a distal inserter portion having an elongate body that defines a hollow interior, the distal inserter portion having an opening for receiving a portion of the proximal handle therein;
   - a locking portion configured to engage a unilateral portion of an implant;
   - a control shaft received in the hollow interior, the control shaft being configured to translate distally to engage the implant engaged by the locking portion; and
   - a knob configured to engage a proximal end of the control shaft to translate the control shaft relative to the distal inserter portion to transition the locking portion from an unlocked configuration to a locked configuration to secure the locking portion to the implant.
2. The surgical instrument of example 1, wherein the locking portion further comprises a retractable clasp that slides along a surface of the implant during distal translation of the control shaft to engage a groove formed therein.

3. The surgical instrument of example 2, wherein the locked configuration further comprises pulling the retractable clasp upward and inward to force a proximal-facing bearing surface of the clasp against a distal-facing bearing surface of the implant.

4. The surgical instrument of any of examples 1 to 3, wherein the locking portion further comprises one or more insertion tabs and a stop beam, the insertion tabs engaging a surface of the implant to lock thereto and the stop beam configured to abut the implant to prevent further translation of the control shaft.

5. The surgical instrument of any of examples 1 to 4, wherein the distal inserter portion includes one or more attachment features extending therefrom that are configured to be received in an auxiliary instrument for coupling thereto.

6. The surgical instrument of example 5, wherein the one or more attachment features further comprise one or more pins that extend from the body of the distal inserter portion.

7. The surgical instrument of example 5, further comprising a reducer instrument that engages the one or more attachment features, the reducer instrument having a reducer shaft received within a housing to reduce a spinal rod into the implant.

8. The surgical instrument of example 7, wherein the housing further comprising one or more arms that extend therefrom, the arms having one or more tracks for receiving the one or more attachment features therein.

9. The surgical instrument of example 7, wherein the reducer instrument further comprises a retaining lever coupled to the housing to facilitate locking of the reducer instrument to the one or more attachment features.

10. The surgical instrument of example 9, wherein the retaining lever is configured to pivot relative to the housing to lock the reducer instrument to the distal inserter portion.

11. The surgical instrument of example 7, wherein the reducer shaft comprises a drive interface configured to couple to an adapter for moving the reducer shaft relative to the housing.

12. The surgical instrument of example 7, wherein the reducer shaft includes a proximal threaded portion and a distal translating portion, wherein rotation of the proximal threaded portion translates the distal portion into engagement with the spinal rod.

13. The surgical instrument of example 12, wherein the instrument provides a counter torque during spinal rod reduction.

14. A surgical instrument, comprising:
- a proximal handle;
- a longitudinal shaft coupled to the handle; and
- an engagement feature disposed on a distal end of the shaft to engage one or more features of an implant, a sidewall of the engagement feature defining a distally-facing recess and having an inner threaded surface configured to couple to a corresponding feature of the implant to couple the shaft to the implant.

15. The instrument of example 14, wherein the sidewall has an outer threaded surface configured to couple to a corresponding feature of the implant to couple the shaft to the implant.

16. The instrument of example 15, wherein the inner threaded surface and the outer threaded surface are located on opposed surfaces of the sidewall.

17. The instrument of example 16, wherein the inner threaded surface and the outer threaded surface are axially offset such that a distal end of the outer threaded surface is positioned proximal to a proximal end of the inner threaded surface.

18. The instrument of example 17, wherein the sidewall tapers distally starting distal to the outer threaded surface.

19. The instrument of any of examples 14 to 18, wherein the sidewall tapers distally starting proximal to the inner threaded surface.

20. The instrument of any of examples 14 to 19, wherein the engagement feature further comprises a centering pin that extends distally from the engagement feature, the centering pin being configured to be received in a portion of the implant.

21. A surgical method, comprising:
- bringing a holder instrument into contact with an implant, the holder instrument having a longitudinal shaft that includes an engagement surface on a distal end thereof, the engagement surface having a reduced diameter portion with inner threads;
- threading the holder instrument into a first corresponding feature of the implant, the first corresponding feature being a surface that corresponds with the inner threads; and
- positioning the implant relative to a surgical site using the holder instrument.

22. The method of example 21, wherein the distal end of the holder instrument further comprises outer threads and the method further comprises:
- decoupling the holder instrument from the first corresponding feature; and
- threading the holder instrument into a second corresponding feature of the implant, the second corresponding feature being a surface that corresponds with the outer threads.

23. The method of example 22, wherein the second corresponding feature comprises inner threads formed within a recess of the implant.

24. The method of any of examples 21 to 23, wherein threading the holder instrument into the first corresponding feature further comprises engaging outer threads of a set screw with the inner threads.

25. The method of example 24, wherein a centering pin of the engagement surface is distally advanced into a recess of the set screw.

26. A surgical method, comprising:
- coupling an inserter instrument to an implant having opposed arms that define a recess such that the inserter instrument contacts only one of the opposed arms and maintains access to the recess;
- positioning the implant relative to a surgical site using the inserter instrument such that at least a portion of a fixation element is disposed within the recess of the implant;
- inserting a set screw into the implant to capture the fixation element within the recess of the implant while maintaining a position of the implant using the inserter instrument.

27. The method of example 26, further comprising tightening the set screw by rotating the set screw in a first direction relative to the implant while imparting a counter-torque force to the implant using the inserter instrument.
28. The method of any of examples 26 to 27, further comprising decoupling the inserter instrument from the implant.

What is claimed is:

1. A surgical instrument comprising:

a proximal handle;

a distal inserter portion having an elongate body that defines a hollow interior, the distal inserter portion having an opening for receiving a portion of the proximal handle therein;

a locking portion configured to engage a unilateral portion of an implant;

a control shaft received in the hollow interior, the control shaft being configured to translate proximally and distally to engage the implant engaged by the locking portion;

a knob configured to engage a proximal end of the control shaft to translate the control shaft relative to the distal inserter portion to transition the locking portion from an unlocked configuration to a locked configuration to secure the locking portion to the implant; and a spring disposed between the elongate body and the knob, the spring being configured to exert a proximally-directed biasing force onto the control shaft;

wherein, absent actuation of the knob to distally drive the control shaft the spring maintains the control shaft in a provisional locking position to provisionally engage the implant.

2. The surgical instrument of claim 1, wherein the locking portion further comprises a retractable clasp that slides along a surface of the implant during proximal translation of the control shaft to engage a groove formed therein.

3. The surgical instrument of claim 2, wherein the locked configuration further comprises pulling the retractable clasp upward and inward to force a proximal-facing bearing surface of the clasp against a distal-facing bearing surface of the implant.

4. The surgical instrument of claim 1, wherein the locking portion further comprises one or more insertion tabs and a stop beam, the insertion tabs engaging a surface of the implant to lock thereto and the stop beam configured to abut the implant to prevent further translation of the control shaft.

5. The surgical instrument of claim 1, further comprising a reducer instrument that engages the distal inserter portion, the reducer instrument having a reducer shaft received within a housing to reduce a spinal rod into the implant.

6. The surgical instrument of claim 5, wherein the housing further comprising one or more arms that extend therefrom for receiving the distal inserter portion therebetween.

7. The surgical instrument of claim 5, wherein the reducer instrument further comprises a retaining lever coupled to the housing to facilitate locking of the reducer instrument.

8. The surgical instrument of claim 7, wherein the retaining lever is configured to pivot relative to the housing to lock the reducer instrument to the distal inserter portion.

9. The surgical instrument of claim 5, wherein the reducer shaft comprises a drive interface configured to couple to an adapter for moving the reducer shaft relative to the housing.

10. The surgical instrument of claim 5, wherein the reducer shaft includes a proximal threaded portion and a distal translating portion, wherein rotation of the proximal threaded portion translates the distal translating portion into engagement with the spinal rod.

11. The surgical instrument of claim 10, wherein the surgical instrument provides a counter torque during spinal rod reduction.

12. The surgical instrument of claim 1, further comprising a track that extends through an entire thickness of the distal inserter portion, the thickness being defined along a plane that lies parallel to a plane in which a central longitudinal axis of the distal inserter portion extends.

13. The surgical instrument of claim 12, wherein the track is angled relative to the central longitudinal axis of the distal inserter portion such that a distal end of the control shaft is configured to translate in a first direction during distal translation.

14. The surgical instrument of claim 1, wherein the knob is configured to distally translate the control shaft to overcome the provisional locking force to secure the locking portion to the implant.

15. A surgical instrument comprising:

a proximal handle;

a distal inserter portion having an elongate body that defines a hollow interior, the distal inserter portion having an opening for receiving a portion of the proximal handle therein, with the distal inserter portion being defined by: i) a width, and ii) a thickness that is perpendicular to the width and larger than the width;

a locking portion configured to engage a unilateral portion of an implant;

a control shaft received in the hollow interior, the control shaft being configured to translate proximally and distally to engage the implant engaged by the locking portion;

a knob configured to engage a proximal end of the control shaft to translate the control shaft relative to the distal inserter portion to transition the locking portion from an unlocked configuration to a locked configuration to secure the locking portion to the implant; and a track that extends through an entire thickness of the distal inserter portion.

16. The surgical instrument of claim 15, wherein the track is angled relative to the central longitudinal axis of the distal inserter portion such that a distal end of the control shaft is configured to translate in a first direction during distal translation.

17. The surgical instrument of claim 15, wherein the locking portion further comprises a retractable clasp that slides along a surface of the implant during proximal translation of the control shaft to engage a groove formed therein.

18. The surgical instrument of claim 17, wherein the locked configuration further comprises pulling the retractable clasp upward and inward to force a proximal-facing bearing surface of the clasp against a distal-facing bearing surface of the implant.

* * * * *